United States Patent
Ghosal et al.

(10) Patent No.: US 8,962,576 B2
(45) Date of Patent: Feb. 24, 2015

(54) COMPOSITIONS AND METHOD FOR IMPROVING ENDOTHELIAL FUNCTION AND CARDIOVASCULAR HEALTH

(71) Applicant: Natreon, Inc., New Brunswick, NJ (US)

(72) Inventors: Shibnath Ghosal, Kolkata (IN); Muruganandam Veeraragavan, Kolkata (IN); Sanyasi R. Kalidindi, East Brunswick, NJ (US)

(73) Assignee: Natreon, Inc., New Bruswick, NJ (US)

( * ) Notice: Subject to any disclaimer, the term of this patent is extended or adjusted under 35 U.S.C. 154(b) by 55 days.

(21) Appl. No.: 13/850,911

(22) Filed: Mar. 26, 2013

(65) Prior Publication Data

US 2013/0261068 A1  Oct. 3, 2013

Related U.S. Application Data

(60) Provisional application No. 61/618,289, filed on Mar. 30, 2012.

(51) Int. Cl.

| | | |
|---|---|---|
| *A01N 43/04* | (2006.01) | |
| *A61K 31/70* | (2006.01) | |
| *A61K 31/7048* | (2006.01) | |
| *A61K 31/366* | (2006.01) | |
| *A61K 31/365* | (2006.01) | |
| *A61K 36/47* | (2006.01) | |

(52) U.S. Cl.
CPC ........... *A61K 31/7048* (2013.01); *A61K 31/366* (2013.01); *A61K 31/365* (2013.01); *A61K 36/47* (2013.01)
USPC .............................................. 514/27; 514/32

(58) Field of Classification Search
None
See application file for complete search history.

(56) References Cited

U.S. PATENT DOCUMENTS

| | | |
|---|---|---|
| 6,124,268 A | 9/2000 | Ghosal |
| 6,290,996 B1 | 9/2001 | Ghosal |
| 6,362,167 B1 | 3/2002 | Ghosal |

OTHER PUBLICATIONS

Mehta et al. Pharmaceutical Biology (2009), vol. 47, pp. 1050-1055.*
Suryanarayana et al. Molecular Vision (2007), vol. 13, pp. 1291-1297.*
Akhtar, M.S., et al., Effect of Amla fruit (*Emblica officinalis* Gaertn.) on blood glucose and lipid profile of normal subjects and type 2 diabetic patients, Int. J. Food Sci. Nutr. (2011) 62(6): 609-616 (Abstract Only).
Anila, L., et al., Flavonoids from *Emblica officinalis* and *Mangifera indica*—effectiveness for dyslipidemia, J. Ethnopharmacol. (2002) 79: 81-87 (Abstract Only).
Antony, B., et al., A Pilot Clinical Study to Evaluate the Effect of *Emblica officinalis* Exatract (AMLAMAXTM) on Markers of Systemic Inflammation and Dyslipidemia, Indian J. Clin. Biochem. (2008) 23(4): 378-381.
Beckman, Pathophysiology of Vascular Dysfunction in Diabetes, Cardiology Rounds (2004) 8(10):1-6.
Inzucchi, Oral Antihyperglycemic Therapy for Type 2 Diabetes, JAMA (2002) 287(3):360-372.
Pandolfi, A., et al., Chronic hyperglycemia and nitric oxide bioavailability play a pivotal role in pro-atherogenic vascular modifications, Genes Nutr. (2007) 2:195-208.

* cited by examiner

*Primary Examiner* — Patrick Lewis
(74) *Attorney, Agent, or Firm* — Amin Talati & Updahye LLC; George M. Carrera; Brent A. Batzer

(57) ABSTRACT

Compositions of natural antioxidants, especially those derived from *Phyllanthus emblica* and *Withania somnifera*, and combinations thereof, are provided. The compositions may be used for improvement of endothelial function and cardiovascular health, including treatment of diabetes.

20 Claims, 11 Drawing Sheets

US 8,962,576 B2

COMPOSITIONS AND METHOD FOR IMPROVING ENDOTHELIAL FUNCTION AND CARDIOVASCULAR HEALTH

This application claims the benefit of earlier filed U.S. Provisional Application No. 61/618,289, filed on Mar. 30, 2012, which is hereby incorporated by reference herein.

FIELD OF THE INVENTION

The present invention relates to improvement of endothelial function and cardiovascular health by using compositions of natural antioxidants, especially those derived from *Phyllanthus emblica* and *Withania somnifera*, and combinations thereof. This invention also relates to a method of improving endothelial function and cardiovascular health using such compositions.

BACKGROUND

Cardiovascular disease (CVD) is the number one cause of death globally. More people die annually from CVD than from any other cause. Smoking, hypertension, high LDL cholesterol, low HDL cholesterol and diabetes mellitus (DM) are the five major risk factors for CVD. Diabetes is associated with an increased risk of atherosclerosis, which may result in coronary artery disease (CAD) (A. Pandolfi, et al., "Chronic hyperglycemia and nitric oxide bioavailability play a pivotal role in proatherogenic vascular modifications," *Genes & Nutrition* (2007) 2 (2): 195-208). Physiological impairments that link DM with a marked increase in atherosclerotic vascular disease include platelet hyper-reactivity, a tendency for negative arterial remodeling, impaired fibrinolysis, increased inflammation, and endothelial dysfunction.

Endothelial dysfunction, present at disease onset, may be the cause of atherogenesis that is present throughout the course of DM and associated with late-stage adverse outcomes (Panwar, et al., "Atherothrombotic risk factors & premature coronary heart disease in India: A case-control study," *Indian J. Med. Res.* (July 2011) 134: 26-32). The endothelial dysfunction results from reduced bioavailability of the vasodilator nitric oxide (NO) mainly due to accelerated NO degradation by reactive oxygen species (J. A. Beckman, "Pathophysiology of Vascular Dysfunction in Diabetes," *Cardiology Rounds* (December 2004) Volume 8, Issue 10). A currently favored hypothesis is that oxidative stress, through a single unifying mechanism of superoxide production, is the common pathogenic factor leading to insulin resistance, β-cell dysfunction, impaired glucose tolerance (IGT) and ultimately to Type 2 DM (T2DM). Furthermore, this mechanism has been implicated as the underlying cause of both the macrovascular and microvascular complications associated with Type 2 DM. It follows that therapies aimed at reducing oxidative stress would benefit both patients with T2DM and those at risk for developing diabetes (Potneza, et al., "Endothelial Dysfunction in Diabetes: From Mechanism to Therapeutic Targets," *Current Medicinal Chemistry* (2009) 16: 94-112; S. E. Inzucchi, "Oral Antihyperglycemic Therapy for Type 2 Diabetes. Scientific Review and Clinical Applications," *Journal of American Medical Association* (Jan. 16, 2002—Vol 287, No. 3, pp. 360-372; and Wright, et al., "Oxidative stress in type 2 diabetes: the role of fasting and postprandial glycaemia," *Int. J. Clin. Pract.* (2006 March) 60(3): 308-314).

Many herbs possess potent antioxidant, anti-inflammatory and cardio-protective properties and are used by patients with increased risk of cardiovascular morbidity and mortality in order to treat or prevent disease and/or reduce symptoms. Among them, *Phyllanthus emblica*, syn. *Emblica officinalis* Gaertn., the Indian gooseberry (PE, "Amla") is widely used in Indian medicine for the treatment of various diseases. There are studies which show significant anti-hyperglycaemic and lipid lowering effects of PE in diabetic patients. In in-vitro and animal studies, PE demonstrates potent antioxidant effects against several test systems such as superoxide radical and hydroxyl radical scavenging action, and in systemic augmentation of antioxidant enzymes in animals (Antony, et al., "A pilot clinical study evaluate the effect of *Emblica officinalis* extract (Amlamax™) on markers of systemic inflammation and dyslipidemia," *Indian J. Clin. Biochemistry* (2008) 23(4): 378-381).

*Withania somnifera* (WS, Ashwagandha) is also widely used in Ayurvedic medicine for the treatment of various diseases. WS is an adaptogen and a rejuvenative that helps maintain proper nourishment of the tissues, particularly muscle and bone, while supporting the proper function of the adrenals and reproductive system. Although its therapeutic potential for immunumodulatory, adaptogenic, antioxidant, hypoglycemic and anticancer activities have been reported, very few studies assessing its cardio-protective potential are presently available (Malhotra, et al., "Studies on *Withania somnifera* (Part III). The effect of total alkaloid (Ashwagandholine) on CVS and respiration," *Ind. J. Med. Res.* (1961) 49: 449; Lavie, et al., "Constituents of *Withania somnifera* Dun IV," *J. Chem. Soc.* (1965) 12: 7517; and Dhuley, et al., "Adaptogenic and cardioprotective action of ashwagandha on rats and frogs," *J. Ethnopharmacol.* (2000) 70: 57-63). There are clinical studies which have demonstrated the efficacy of WS in the treatment of hypercholesterolemia.

In view of the above, it would be desirable to provide a potent and therapeutically effective *Phyllanthus emblica* and/or *Withania somnifera* composition for use as a nutritional supplement.

If a way could be found to use a therapeutically effective amount of *Phyllanthus emblica* and/or *Withania somnifera* in a composition to treat or prevent endothelial dysfunction and/or diabetes, this would represent a useful contribution to the medical arts.

SUMMARY OF THE INVENTION

An objective of the present invention is to develop *Phyllanthus emblica* and/or *Withania somnifera* compositions for improving endothelial function and cardiovascular health in patients with Type 2 diabetes mellitus as well as in healthy subjects.

A method of treating or preventing endothelial dysfunction is provided including administering to an individual in need thereof an effective amount of a composition comprising an extract of *Phyllanthus emblica* and a pharmaceutically acceptable carrier, wherein endothelial function is improved.

Other embodiments are contemplated for the effective treatment of human patients having type 2 diabetes mellitus (T2DM). In one embodiment, a method of treating a diabetic individual suffering from type 2 diabetes mellitus includes administering to an individual in need thereof an effective amount of an extract of *Phyllanthus emblica* wherein endothelial function is improved as measured in the levels of one or more markers of oxidative stress and/or inflammation.

In another embodiment, a method of treating a diabetic individual suffering from type 2 diabetes mellitus includes administering to an individual in need thereof an effective amount of an extract of *Phyllanthus emblica* wherein a blood lipid parameter is improved, or one or more cardiovascular parameters is improved.

DETAILED DESCRIPTION

Figure 1:
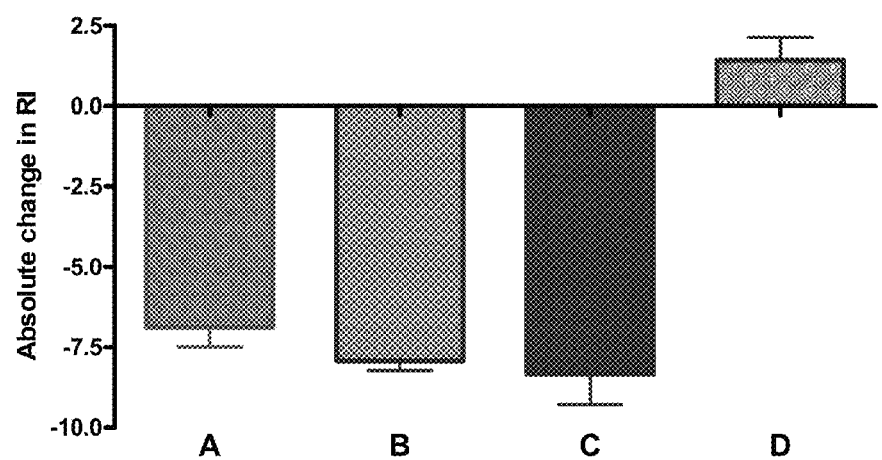
FIG. 1 illustrates absolute change in reflective index (RI %) in type 2 diabetic individuals before and after 12 weeks treatment in one embodiment in accordance with the present invention with an extract of *Phyllanthus emblica*, or atorvastatin, as described in Table X-A.

The following references are hereby incorporated by reference in their entirety, U.S. Pat. Nos. 6,124,268, 6,290,996, and 6,362,167. These references describe the isolation or preparation of extracts and extract blends as used herein.

In one aspect, the present invention reveals the usefulness of *Phyllanthus emblica* and *Withania somnifera* and compositions prepared using at least one of the aforementioned herbs, in improving endothelial function and cardiovascular health in patients with Type 2 diabetes mellitus as well as in healthy subjects.

One suitable composition used herein is an extract blend which is isolated in stable form from the fruit of the *Phyllanthus emblica* plant, as described in detail in U.S. Pat. No. 6,124,268. The extraction process includes treating the finely-pulped fruit with a dilute aqueous or alcoholic-water salt solution, e.g. a 0.1 to 5% (w/w) sodium chloride solution, or the like, preferably at about 70° C.±5° C., or with a buffer solution, e.g. 0.1 to 5% (w/w) of sodium citrate/citric acid, or the like, filtering and drying, to provide the extract in powder form.

The extract includes the active constituents Emblicanin-A and Emblicanin-B, which are gallic/ellagic acid derivatives of 2-ketoglucono-δ-lactone, in an amount by weight of about 35-55%, as well as: Punicagluconic acid, also named punigluconin (about 4-15% by weight), Pedunculagin (about 10-20% by weight), Rutin (about 5-15% by weight), and low-to-medium molecular weight tannoids of gallic/ellagic acid (about 10-30% by weight), gallic acid (up to about 5% by weight), and ellagic acid (up to about 5% by weight). Note that taken together, the overall extracted mixture or blend comprises an isolatable, identifiable, and purifiable group of components comprising a group of low molecular weight hydrolyzable tannoids ("LMwHTs"), generally excluding free gallic acid and ellagic acid. The composition may further include a nutraceutically or pharmaceutically acceptable carrier.

In one suitable embodiment, the amount of LMwHTs contained in a purified and/or enriched extract of *Phyllanthus emblica* is at least about 60% by weight. In another embodiment, the amount of LMwHTs contained in a purified and/or enriched extract of *Phyllanthus emblica* is greater than about 60% by weight. In another embodiment, the amount of LMwHTs contained in a purified and/or enriched extract of *Phyllanthus emblica* is greater than about 70% by weight. CAPROS (available from Natreon, Inc., New Brunswick, N.J.) is one such exemplary extract of *Phyllanthus emblica*.

Patients with diabetes have vascular complications and endothelial dysfunction is one of the early prognostic markers of atherosclerosis which may eventually result in cardiovascular disease. Studies have reported that endothelial dysfunction occurs in patients with diabetes much earlier than clinical manifestations of diabetic vascular complications (Schalkwijk, et al., "Vascular complications in diabetes mellitus: the role of endothelial dysfunction," *Clinical Science* (2005) 109: 143-159). Diabetes is associated with accelerated atherosclerosis and microvascular complications are a major cause of morbidity and mortality, as discussed above. Endothelial cell dysfunction is emerging as a key component in the pathophysiology of cardiovascular abnormalities associated with diabetes mellitus.

Increased arterial stiffness, as measured by pulse wave analysis, is associated with cardiovascular risk factors and established coronary artery disease. Pulse wave analysis is simple and reproducible to stratify cardiac risk in diabetes. Whilst arterial compliance is determined predominantly by structural factors, the vascular endothelium is also involved. The vascular endothelium contributes to vascular tone and endothelial dysfunction is implicated as an early functional alteration predating structural changes of the vasculature.

Conventional cardiac risk factors such as dyslipidemia, hypertension, smoking, and Type 2 diabetes are associated with impaired endothelial function. The intact endothelium promotes vasodilatation principally via the release of NO—originally also called endothelium derived relaxing factor. Endothelium dependent vasodilators reduce pulse wave velocity suggesting nitric oxide (NO) plays a role in determining arterial distendability. Free radical NO has emerged as a fundamental signaling device regulating virtually every critical cellular function and is a potent mediator of cellular damage in many conditions. Nitric oxide is produced in endothelial cells from the substrate L-Arginine via endothelial Nitric oxide synthatase (eNOS). Elevated asymmetric dimethylarginine levels cause coupling, a mechanism which leads to decreased NO bioavailability. The endothelial dysfunction associated with diabetes has been attributed to lack of bioavailable nitric oxide due to reduced ability to synthesize NO from L-Arginine. New basic research insights provide possible mechanisms underlying the impaired NO bioavailability in Type 2 diabetes.

Use of herbs for the treatment of cardiovascular diseases and diabetes in Ayurveda, Chinese and Unani systems of medicine has provided a new lead to understanding the pathophysiology of these diseases. Therefore, it is rational to use our natural resources for identifying and selecting inexpensive and safer approaches for the management of cardiovascular disease along with current therapy. The roots of *Withania somnifera* (ashwagandha, WS), are reported to have extensive therapeutic potential having immune-modulatory, antioxidant, hypoglyceamic and anticancer activity. One study suggests that multiple mechanisms may be responsible for the cardioprotective effect of WS (Mohanty, et al., "Mechanisms of Cardioprotective Effect of *Withania somnifera* in Experimentally Induced Myocardial Infarction," *Basic & Clinical Pharmacology & Toxicology* (2004) 94: 184-190.

Oxidative stress induced by reactive oxygen species (ROS) also plays an important role in the etiology of atherosclerosis and coronary heart disease. Recent research has suggested that oxidative stress is one of the mechanisms involved in endothelial dysfunction. Wide spread attention has been focused on involvement of oxygen free radicals in pathogenesis of diabetes. Cellular enzymatic (e.g., superoxide dismutase or "SOD") and non enzymatic antioxidants (glutathione or "GSH") act as primary line of defense to cope with the deleterious effect of these radical species. Earlier studies showed the beneficial effects of Amla on atherosclerosis and dyslipidemia (Antony, et al.).

Hypercholesterolemia is a major risk factor for the development of atherosclerosis and is associated with coronary and peripheral vascular disease. Several lines of evidences show that the improvement and incidence of coronary artery disease (CAD) is associated with lowering hypercholesterolemia. To treat hypercholesterolemia, extensive interventions are recommended including diet control, exercise and the use of hypocholesterolemic drugs. However some patients cannot tolerate the adverse events from these drugs, such as liver damage which necessitates the use of other safer and efficacious alternative medications. One research group evaluated the anti-hyperglycemic and lipid lowering properties of *Phyllanthus emblica* in normal and diabetic human volunteers (Akhtar, et al., "Effect of Amla fruit (Emblica officinalis Gaertn.) on blood glucose and lipid profile of normal subjects and type 2 diabetic patients," *Int. J. Food Sci. Nutr.* (2011) 62(6): 609-616). In this study, significant decreases were observed in total cholesterol (TC) and triglycerides (TG), and increases were observed in high density lipoprotein-cholesterol (HDL-C) in normal and diabetic volunteers receiving 2 or 3 g of *Phyllanthus emblica* powder per day. In another study of *Phyllanthus emblica* significant reduction in TC, LDL (low density lipoprotein) and TG was reported, whereas there was significant elevation of HDL (high density lipoprotein) (Antony, et al.). The results of their study at doses of 500 mg/day and 1000 mg/day brought significant reduction in the level of risk factors arising from dyslipidemia and inflammation. The exact mechanism by which the fruit of *P. emblica* exerts a beneficial effect is presently not clear. Without intending to be bound by theory, it is believed that *P. emblica*, like statins, possesses HMG CoA reductase inhibitory activity. Thus, *P. emblica* is believed to exert beneficial effects on cardiovascular parameters (Anila, et al., "Flavonoids from *Emblica Officinalis* and *Mangifera indica*-effectiveness for dyslipidemia," *J. Ethnopharmacol.* (2002) 79:81-7). In another recent study, the research group evaluated the hypoglycemic and hypolipidemic effects of extracts of *Withania somnifera* root and leaves in Alloxan-induced diabetic rats and found them to be effective (Udaykumar, et al., "Hypoglycaemic and Hypolipidemic effects of *Withania sominifera* root and leaf extracts on alloxan—induced diabetic rats," *Int. J. Mol. Sci.* (2009) 10: 2367-2382).

EXAMPLES

Two types of human clinical studies were carried out: (a) a randomized, double-blind, parallel and placebo-controlled as well as positive-controlled study in subjects with Type 2 diabetes with a 12 week treatment period, and (b) a randomized, double-blind, placebo-controlled cross-over study in healthy subjects with a 2 week treatment period to evaluate the effect of *Phyllanthus emblica* on cardiovascular changes induced by (i) cold pressor test, and (ii) mental stress test. In study (a), endothelial function is compromised, as discussed above. In study (b), endothelial dysfunction is induced, as disclosed herein.

Study (a) in Type 2 Diabetic Subjects

Study (a) design. Patients of either sex, aged 18-75 years, fasting plasma glucose of ≥110 mg/dL, a glycosylated hemoglobin (HbA1c) between 7% and 10% and taking stable doses of anti-diabetic treatment for the past 8 weeks prior to the screening visit; and having endothelial dysfunction defined as ≤6% change in reflection index (RI) on post salbutamol challenge test were included in the study. Patients with severe uncontrolled hyperglycaemia, uncontrolled hypertension, cardiac arrhythmia, impaired hepatic or renal function, history of malignancy or stroke, smoking, chronic alcoholism, any other serious disease requiring active treatment and treatment with any other herbal supplements, were excluded from the study. Pregnant and lactating women were also excluded.

All the eligible subjects were randomized to receive either one of the four treatments for duration of 12 weeks. There were ten (10) subjects per group. Group 1: one capsule of *Withania somnifera* (Sensoril®) 250 mg twice daily; Group 2: one capsule of *Phyllanthus emblica* (Capros®) 250 mg twice daily; Group 3: one capsule of placebo in the morning and one capsule of Atorvastatin 10 mg at night; or Group 4: one capsule of placebo twice daily. Subjects were asked to revisit for follow up at 4, 8 and 12 weeks of therapy. At each visit they were evaluated for efficacy and safety. Pharmacodynamic evaluation for endothelial function was conducted at every visit. Blood samples were collected for evaluation of biomarkers before and at the end of treatment. Safety lab investigations were conducted before and at the end of the study and as and when required in case of any adverse drug reaction (ADR). Subjects were examiner and/or surveyed for the presence of ADR and the same was recorded in the case report form. Compliance was assessed by pill count method.

The active ingredients used in the capsules have the following compositions.

Sensoril® (available from Natreon, Inc., New Brunswick, N.J.) is a standardized extract of *Withania somnifera*, containing not less than 8% withanolide glycosides, not more than 2.0% Withaferin-A, not less than 32% oligosaccharides, not more than 0.5% alkaloids and not more than 10% polysaccharides.

Capros® (available from Natreon, Inc., New Brunswick, N.J.) is a standardized extract of *Phyllanthus emblica* containing at least 60% low molecular weight hydrolysable tannins, including Emblicanin-A, Emblicanin-B, Punigluconin and Pedunculagin as active ingredients.

Procedure for Assessment of Endothelial Function by Determination of Reflection Index (RI).

A salbutamol (albuterol) challenge test employing digital volume plethysmography was used to assess endothelial function as reported by Chowienczyk et al., "Photoplethysmographic assessment of pulse wave reflection: blunted response to endothelium dependant beta 2-adrenergic vasodilation in type 2 diabetes mellitus," *J. Am. Coll. Cardiol*. (1999 December) 34(7):2007-14; and Naidu, et al., "Comparison of two $\beta_2$ adrenoceptor agonists by different routes of administration to assess human endothelial function," *Indian J. Pharmacol*. (2007) 39:168-9. The patients were examined in supine position after 5 minutes of rest. A digital volume pulse (DVP) was obtained using a photo plethysmograph (Pulse Trace PCA2, PT200, Micro Medical, Gallingham, Kent, UK) transmitting infrared light at 940 nm, placed on the index finger of the right hand. The signal from the plethysmograph was digitized using a 12 bit analogue to digital converter with a sampling frequency of 100 Hz. DVP waveforms were recorded over 20 second period and the height of the late systolic/early diastolic portion of the DVP was expressed as a percentage of the amplitude of the DVP to yield the reflection index (RI), per the procedure described in detail by Millasseau et al., "Determination of age related increases in large artery stiffness by digital pulse contour analysis," *Clinical Science* (2002) 103: 371-377. Three DVP recordings were taken, and measurements of reflection index (RI) were calculated and the mean value was determined. Patients were then administered 400 μg of salbutamol by inhalation. After 15 minutes three measurements of RI were obtained again and the difference in mean RI before and after administration of salbutamol was used for assessing endothelial function. A change of ≤6% in RI post-salbutamol was considered as endothelial dysfunction. Results are presented in Tables III and IV below.

Biomarker Evaluation.

Malondialdehyde (MDA) levels were determined as described in Vidyasagar, et al., "Oxidative stress and antioxidant status in acute organophosphorous insecticide poisoning," *Indian J. Pharmacol*. (April 2004) 36(2): 76-79. Glutathione levels were determined as described in G. L. Ellman, *Arch. Biochem. Biophys*. (1959) 82: 70-77 (original determination). Nitric oxide levels were estimated spectrophotometrically as described in Miranda, et al., "A Rapid, Simple Spectrophotometric Method for Simultaneous Detection of Nitrate and Nitrite," *NITRIC OXIDE: Biology and Chemistry* (2001) Vol. 5, No. 1, pp. 62-71. The results of these assays are presented in Tables III and IV below.

Evaluation of Platelet Aggregation.

The platelet aggregation was determined by the following procedure using Wheecon chronologue dual channel platelet aggregometer (Wheecon Instruments Pvt. Ltd., Chemai, Tamilnadu, India). The percentage decrease in platelet aggregation was recorded at baseline and 3 hours post treatment. Approximately 9 ml of blood sample was collected in a 10 ml plastic test tube containing 1 ml of 3.8% Sodium Citrate from the cubital vein of the subject at baseline and after 3 hours post treatment in all the groups. The test was performed immediately within a time period of one and half hours from collection. The samples were centrifuged at 800 rpm for 15 minutes to obtain a platelet-rich plasma. A portion of the same sample was centrifuged at 2500 rpm for 10 minutes so as to get a platelet-poor plasma sample. The aggregometer was switched about 30 minutes before the test to allow the heating block to warm up to 37° C. Then the test was performed in duplicate by taking 0.5 ml of platelet-rich plasma using 5 μl of adenosine di-phosphate (ADP) solution (2 μgm/ml) in cuvettes containing magnetic stir bars. The speed of stir bars were adjusted at 1200 rpm so as to facilitate the aggregation of the platelets. The platelet-poor plasma sample was kept as reference. The readings were recorded at baseline and after treatment with ADP. The percentage aggregation at baseline and the percentage inhibition of platelet aggregation on post treatment with all the four treatments was calculated.

Safety Assessments.

All the subjects had undergone complete physical examination, safety lab evaluations at baseline, i.e., prior to treatment, and at the end of the treatment. Samples were collected after an overnight fast of 12 hrs after the last dose of medication for determination of haemoglobin level, glycosylated hemoglobin (HbA1c), urea and creatinine levels, liver function, and lipid profile (total cholesterol, high density lipoprotein cholesterol (HDL-C), and low density lipoprotein cholesterol (LDL-C)). Plasma glucose, liver function test, blood urea, serum creatinine and HbA1c were measured using appropriate standard techniques.

Efficacy Parameters.

The primary efficacy measure was a change in endothelial dysfunction assessed by more than 6% change in reflection index at 12 weeks as observed among the treatment groups. Secondary efficacy measures include changes in oxidative stress markers, serum levels of nitric oxide at 12 weeks as observed among the treatment groups, and also evaluation of safety and tolerability of the test medications.

Data Analysis.

Data are presented as mean±SD. ANOVA and tailed unpaired t-test was performed for between groups analysis while within group analysis was performed using the paired t-test. A p-value <0.05 was considered to be statistically significant. All statistical analyses were performed using the SAS version 9.1.3® (SAS Institute, Inc., Cary, N.C.).

Results of Study (a).

Ten subjects in each group completed the study. Detailed demographic characteristics of the four study groups are shown in Table I. There was no significant difference between treatment groups in baseline characteristics including age, body mass index and lipid profile.

TABLE I

Type 2 Diabetic Subjects; Demographic characteristics of all study groups

| Parameter | Placebo | Withania somnifera | Phyllanthus emblica | Atorvastatin |
|---|---|---|---|---|
| Total No. Test Subjects | 10 | 10 | 10 | 10 |
| Age | 58.20 ± 11.97 | 58.40 ± 10.36 | 59.60 ± 6.91 | 59.40 ± 12.22 |
| Sex( M/F) | 6/4 | 7/3 | 8/2 | 7/3 |
| Weight (Kg) | 69.16 ± 4.33 | 71.46 ± 4.69 | 73.70 ± 6.48 | 72.16 ± 6.68 |
| BMI (Kg/m$^2$) | 24.78 ± 1.07 | 25.82 ± 1.04 | 25.38 ± 0.47 | 26.66 ± 2.74 |

Effects of the test samples on lipid profile are shown in Table II. Compared with baseline, treatment with Sensoril® significantly reduced total cholesterol by about 9% (from 155±33.67 to 141.6±32.02 mg/dl, p<0.001). There was also a significant reduction in total cholesterol by about 11% on treatment with Capros® (from 172.3±17.83 mg/dl to 153.2±16.98 mg/dl, p<0.001), and Atorvastatin (from 185.7±36.38 mg/dl to 146±24.52 mg/dl, p<0.001). After 12 weeks of treatment the LDL-C levels were significantly decreased with Sensoril® by about 20% (from 145.7±50.41 to 115±37.47 mg/dl, <0.001), Capros® by about 29% (from 128.8±34.78 mg/dl to 91.4±17.58 mg/dl, p<0.001), and Atorvastatin (from 133.2±38.09 mg/dl to 87.6±19.07 mg/dl, p<0.001). Similarly significant reduction was observed in triglycerides on treatment with Sensoril® by about 17% (from 165±46.85 mg/dl to 137.6±36.7 mg/dl, p<0.05), Capros® by about 12% (from 132±25.76 mg/dl to 116.7±19.1 mg/dl, p<0.01), and Atorvastatin (from 169.1±67.51 mg/dl to 102.8±40.61 mg/dl, p<0.01). There was no significant change observed in HDL-C levels on treatment with Sensoril® (from 40.4±4.32 mg/dl to 40.2±3.88 mg/dl). However, treatment with Capros® and Atorvastatin significantly increased HDL-C levels (from 40±4.02 mg/dl to 44±6.32 mg/dl, p<0.05, and 42.77±6.13 mg/dl to 48.2±6.01 mg/dl, p<0.05) respectively.

Table III shows the effect of treatments on Reflection Index (RI). A significant improvement in endothelial function was observed in Capros® and Atorvastatin groups compared to baseline. The change in RI post salbutamol being −2.67%±1.53% compared to −7.84%±3.93% with Sensoril® (p<0.01); −2.7%±1.22% compared to −9.43±3.32 with Capros® (p<0.001); and −2.45%±0.64% compared to −11.04%±5.48% with Atorvastatin (p<0.001). However, no change was observed with placebo. Table IV shows the % change in RI index with treatments.

Table III also shows the effect of treatments on endothelial function biomarkers.

Nitric Oxide. With Sensoril® there was no significant improvement in the levels of Nitric oxide (46.87±19.78 μmol/L to 46.26±18.85 μmol/L). Treatment with Capros® and Atorvastatin significantly increased the levels of Nitric oxide from 42.62±13.46 μmol/L to 52.96±14.92 μmol/L, (p<0.01) and from 42.24±6.771 μmol/L to 68.89±11.54 μmol/L, (p<0.001) respectively. The mean percent change in Nitric oxide levels after 12 weeks of treatment with Capros® and Atorvastatin being 28.49%±23.68 and 64.71%±27.25, respectively. Whereas there was no change observed in Nitric oxide levels in Sensoril group when compared to placebo (Table IV).

Malondialdehyde (MDA). Treatment with Sensoril® did not significantly reduce MDA levels (3.38±1.36 nmol/ml to 2.95±0.90 nmol/ml). Treatment with Capros® and Atorvastatin significantly decreased MDA levels from 3.23±1.59 nmol/ml to 2.46±1.21 nmol/ml, (p<0.01) and from 3.48±0.73 nmol/ml to 2.13±0.48 nmol/ml, (p<0.001) respectively. The

TABLE II

Type 2 Diabetic Subjects: Lipid profile data after 12 weeks treatment with Placebo, Withania somnifera (Sensoril ®), Phyllanthus emblica (Capros ®), and Atorvastatin (All values are given as Mean ± SD)
HDL-C—high-density lipoprotein cholesterol; LDL-C—low-density lipoprotein cholesterol.

| | Placebo (n = 10) | | Sensoril (n = 10) | | Capros (n = 10) | | Atorvastatin (n = 10) | |
|---|---|---|---|---|---|---|---|---|
| Parameter | Pre treatment | Post treatment | Pre treatment | Post treatment | Pre treatment | Post treatment | Pre treatment | Post treatment |
| Total Cholesterol (mg/dL) | 168.5 ± 25.57 | 185.5 ± 24.55 | 155 ± 33.67 | 141.6 ± 32.02# | 172.3 ± 17.83 | 153.2 ± 16.98# | 185.7 ± 36.38 | 146 ± 24.52# |
| HDL-C (mg/dL) | 39.40 ± 5.71 | 38.5 ± 6.62 | 40.4 ± 4.32 | 40.2 ± 3.88NS | 40 ± 4.02 | 44 ± 6.32$ | 42.77 ± 6.13 | 48.2 ± 6.01$ |
| LDL-C (mg/dL) | 144.3 ± 41.89 | 158.6 ± 49.76 | 145.7 ± 50.41 | 115 ± 37.47# | 128.8 ± 34.78 | 91.4 ± 17.58# | 133.2 ± 38.09 | 87.6 ± 19.07# |
| Triglycerides (mg/dL) | 160.7 ± 18.02 | 166.9 ± 19.35 | 165 ± 46.85 | 137.6 ± 36.7$ | 132 ± 25.76 | 116.7 ± 19.1* | 169.1 ± 67.51 | 102.8 ± 40.61* |

$p < 0.05 when compared with baseline
*p < 0.01 when compared with baseline
p < 0.001 when compared to baseline
Total Cholesterol - Non significant when compared between the three active treatments
HDL-C - between post treatment with Sensoril ® and Atorvastatin - p < 0.01
LDL-C - Non significant when compared between the three active treatments
Triglycerides - Non significant when compared between the three active treatments mean percent change in Malondiadehyde levels after 12 weeks of treatment with Capros® and Atorvastatin being −21.02%±25.17 and −38.05%±10.43, respectively. Whereas there was no change observed in MDA levels in Sensoril® group when compared to placebo (Table IV).

Glutathione. Treatment with Sensoril® did not significantly improve Glutathione levels (577.9±221.9 µmol/L to 624.8±234.6 µmol/L). Treatment with Capros® and Atorvastatin significantly increased Glutathione levels from 560.1±87.30 µmol/L to 706.6±87.18 µmol/L, ($p<0.01$) and from 530.8±168.4 µmol/L to 721.6±116.9 µmol/L, ($p<0.01$), respectively. The mean percent change in Glutathione levels after 12 weeks of treatment with Capros® and Atorvastatin being 28.54%±25.35 and 51.77%±62.72, respectively. However, there was no change observed in Glutathione levels in Sensoril® group when compared to placebo (Table IV). Also, there was no change observed in the placebo group on post treatment in any of the evaluated parameters.

Platelet aggregation. Table V shows the effect of treatments on inhibition of platelet aggregation. There was a significant inhibition of platelet aggregation after three hours of treatment with Capros® (from 75.65±8.57 to 58.58±9.56, $p<0.001$) and Atorvastatin (from 66.50±11.00 to 62.00±12.81, $p<0.05$) when compared to baseline. The mean percent inhibition in platelet aggregation was found to be 21.25%±11.86 in Capros® and 7.11%±7.94 in Atorvastatin. However, there was no significant percent decrease observed in platelet aggregation 3 hours post treatment with Sensoril and placebo group.

TABLE III

Type 2 Diabetic Subjects: Endothelial function and biomarkers of oxidative stress after 12 weeks treatment with placebo, Sensoril ®, Capros ® and Atorvastatin (All values are given as Mean ± SD)

| | Placebo (n = 10) | | *Withania somnifera* (n = 10) Sensoril ® | | *Phyllanthus emblica* (n = 10) Capros ® | | Atorvastatin (n = 10) | |
|---|---|---|---|---|---|---|---|---|
| Parameter | Pre treatment | Post treatment | Pre treatment | Post treatment | Pre treatment | Post treatment | Pre treatment | Post treatment |
| Abs Change in RI(%) Post Salbutamol challenge) | −2.40 ± 0.96 | −0.10 ± 3.75 | −2.67 ± 1.53 | −7.84 ± 3.93$ | −2.70 ± 1.22 | −9.43 ± 3.32# | −2.45 ± 0.64 | −11.04 ± 5.48# |
| NO (µmol/L) | 43.48 ± 8.472 | 41.12 ± 10.60 | 46.87 ± 19.78 | 46.26 ± 18.85NS | 42.62 ± 13.46 | 52.96 ± 14.92$ | 42.24 ± 6.771 | 68.89 ± 11.54# |
| MDA (nmol/ml) | 3.72 ± 0.52 | 3.74 ± 0.46 | 3.38 ± 1.36 | 2.95 ± 0.90NS | 3.23 ± 1.59 | 2.46 ± 1.21$ | 3.48 ± 0.73 | 2.13 ± 0.48# |
| Glutathione (µmol/L) | 546.6 ± 65.11 | 542.2 ± 66.52 | 577.9 ± 221.9 | 624.8 ± 234.6NS | 560.1 ± 87.30 | 706.6 ± 87.18# | 530.8 ± 168.4 | 721.6 ± 116.9# |

In RI index
$p < 0.001$ when compared with baseline
$$p < 0.01$ when compared with baseline
NS—In RI index Non significant when compared between the three active treatments
In NO Levels
$p < 0.001$ treatments compared with baseline
$p < 0.001$ between Atorvastatin & Sensoril ®
$$p < 0.01$ treatments compared with baseline
$$p < 0.01$ between Capros ® versus Sensoril ® and Atorvastatin
In MDA Levels
$p < 0.001$ Atorvastatin compared with baseline
$$p < 0.01$ Capros ® compared with baseline
*$p < 0.05$ between Sensoril ® and Atorvastatin
NS—non significant treatments compared with baseline, between post treatment Capros ® & Sensoril ® and Capros ® & Atorvastatin
In Glutathione Levels
$p < 0.01$ when compared to baseline
NS—non significant treatments compared with baseline and between the three active treatments

TABLE IV

Type 2 Diabetic Subjects: Mean % change in RI, NO, MDA and Glutathione values after 12 weeks of treatment

| Parameters | Placebo | Sensoril ® | Capros ® | Atorvastatin |
|---|---|---|---|---|
| Abs Change in RI (%) Post Salbutamol challenge | −84.17 ± 161.0 | 196.8 ± 248.4 | 271.4 ± 203.1 | 336.1 ± 235.2 |
| NO (µmol/L, %) | −6.02 ± 11.23 | −0.63 ± 4.93 | 28.49 ± 23.68 | 64.71 ± 27.25 |
| MDA (nmol/ml, %) | 0.69 ± 3.87 | −6.33 ± 24.69 | −21.02 ± 25.17 | −38.05 ± 10.43 |
| Glutathione (µmol/L, %) | −0.84 ± 1.60 | 9.13 ± 15.02 | 28.54 ± 25.35 | 51.77 ± 62.72 |

TABLE V

Type 2 Diabetic Subjects: Percentage decrease in platelet aggregation

| Group | Pre treatment | Post treatment | % Inhibition of Platelet Aggregation |
|---|---|---|---|
| Placebo (n = 10) | 67.80 ± 9.15 | 66.80 ± 6.92 | −3.30 ± 5.32 |
| Atorvastatin (n = 10) | 66.50 ± 11.00 | 62.00 ± 12.81 | 7.11 ± 7.94 * |
| Capros ® (n = 10) | 75.65 ± 8.57 | 58.58 ± 9.56 | 21.25 ± 11.86$ |
| Sensoril ® (n = 10) | 71.10 ± 10.57 | 66.50 ± 10.62 | 6.09 ± 8.57 NS |

$p < 0.001 when compared to baseline
p < 0.01 when compared between Capros ® & Atorvastatin
p < 0.01 when compared between Capros ® & Sensoril ®
* p < 0.05 when compared to baseline
NS—Non significant when compared to baseline and between Atorvastatin & Sensoril ®

Safety parameters. At baseline, vital parameters, renal and hepatic parameters evaluated were within normal limits. Post treatment, there were no significant changes in vital parameters, renal and hepatic functions in any treatment groups. There were no serious adverse events recorded in the study; however, two subjects complained of mild diarrhea, one in Capros® group and the other in Sensoril® group. No subjects were withdrawn from the study because of these adverse events.

Studies (b) in Healthy Subjects

Although healthy subjects may not have cardiovascular risk factors, they may develop cardiovascular changes when subjected to stress. Thus, Capros® was studied to evaluate its effect on the cardiovascular changes induced by cold pressure test and mental stress test in two separate studies. In other words, these studies were intended to induce endothelial dysfunction.

Study (b) Design. A randomized, double blind, multi-dose, crossover and placebo controlled study. Treatment Groups: (1) Capros®: 2×250 mg Capsules BID (total daily dose of 500 mg) for 14 days; (2) Placebo: 2 capsules BID for 14 days.

Ten healthy participants aged 20-30 yrs, were screened. Following a full medical history (including smoking habits) and physical examination, which included hematological and biochemical screening, and an electrocardiogram, volunteers were excluded if there was any evidence of physical illness or drug abuse. Each subject was approached personally and if they agreed to participate, written informed consent was taken after a full explanation of aims, procedures and risks of the study. The study was approved by an Institutional Ethics Committee as described below.

A total of 6 eligible subjects were enrolled and randomized. Training was given prior to the test day to introduce the subjects to the test procedure and to make them familiar with the testing device. All the recordings were carried out during the morning between 7:30 a.m. to 10:00 a.m. after a light breakfast. Six male subjects were enrolled with mean age, height and weight of 24.70±2.12 yrs, 166.6±1.41 cm, 64.35±2.32 kg respectively. All the randomized subjects completed the study and were evaluated for cardiovascular measurements. No subject discontinued the study.

Subjects arrived at the laboratory following an overnight fast including abstinence from caffeine-containing beverages or alcohol for 12 hrs, confirmed by a questionnaire at the beginning of the session. Before any testing, each subject rested in a supine position for 20 min in a quiet, temperature-controlled (26°±1° C.) room. Subjects were asked to breathe normally and to remain still during cardiovascular measurement. Subjects were permitted to listen to music and to read, that is, general relaxation, except during the periods of cardiovascular measurement.

All the test measures were performed at baseline. Then the subject was given study medication and asked to take 2 capsules twice daily for 2 weeks of the study medication allocated to them as per prior randomization schedule with 200 ml of water. The same test was then repeated after two weeks of treatment. All the measurements were recorded 3 hrs post drug administration.

A washout period of 10-14 days was given between the treatments. Subjects then crossed over to receive the second formulation 2 capsules twice daily for 2 weeks. All the same test procedures were repeated before and after treatment.

Brachial blood pressure (BP) and heart rate (HR) were measured with an automated digital BP monitor (OMRAN, SEM-1) and a mean of 3 readings was taken. All readings were taken with cuff placed on the subject's non-dominant arm positioned at heart level with the forearm resting on a table. After determination of BP and resting aortic pressures, the test was performed as per the below mentioned procedure. Measurements of aortic pressure were carried out before and at the end of the cold pressure test (CPT) as described (within 2 min).

Measurement of Wave Reflection Indices

Augmentation index (AIx) and augmented pressure of the central (aortic) pressure waveform were measured as indices of wave reflections. Augmented pressure is the pressure added to the incident wave by the returning reflected one and represents the pressure boost that is caused by wave reflection and with which the left ventricle must cope.

Augmentation pressure (AP) is the contribution that wave reflection makes to systolic arterial pressure, and it is obtained by measuring the reflected wave coming from the periphery to the centre. Reduced compliance of the elastic arteries causes an earlier return of the 'reflected wave', which arrives in systole rather than in diastole, causing a disproportionate rise in systolic pressure and an increase in pulse pressure (PP), with a consequent increase in left ventricular afterload and impaired coronary perfusion.

The augmentation index (AIx) is an indirect measure of arterial stiffness and it is calculated as AP (augmentation pressure) divided by PP×100 to give a percentage. With an increase in stiffness there is a faster propagation of the forward pulse wave as well as a more rapid reflected wave. AP and AIx both increase with age. Augmentation index is commonly accepted as a measure of the enhancement (augmentation) of central aortic pressure by a reflected pulse wave.

Augmentation index can be calculated from pulse waves of the common carotid artery recorded by applanation tonometry (SphygmoCor; AtCor Medical, Sydney, Australia). The systolic part of central arterial waveform is characterized by two pressure peaks. The first peak is caused by left ventricular ejection, whereas the second peak is a result of wave reflection. The difference between both pressure peaks reflects the degree to which central arterial pressure is augmented by wave reflection. Augmentation index (%) is defined as the percentage of the central pulse pressure which is attributed to the reflected pulse wave and, therefore, reflects the degree to which central arterial pressure is augmented by wave reflection.

Augmentation index is a sensitive marker of arterial status, in that:

Augmentation index has been shown to be a predictor of adverse cardiovascular events in a variety of patient populations, and higher augmentation index is associated with target organ damage; and Augmentation index can distinguish between the effects of different vasoactive medications when upper arm blood pressure and pulse wave velocity do not.

The augmentation index (AIx, defined as augmented pressure divided by pulse pressure and expressed as a percentage) is thus a composite measure of the magnitude of wave reflections and arterial stiffness, which affects timing of wave reflections. Because the augmentation index is influenced by changes in heart rate (HR), it is also accordingly corrected (AIx@75). The augmentation index was measured by using a validated, commercially available system (SphygmoCor; AtCor Medical, Sydney, Australia) that employs the principle of applanation tonometry and appropriate acquisition and analysis software for noninvasive recording and analysis of the arterial pulse. In brief, from radial artery recordings, the central (aortic) arterial pressure was derived with the use of a generalized transfer function that has been shown to give an accurate estimate of the central arterial pressure waveform and its characteristics. Waveforms of radial pressure were calibrated according to sphygmomanometric systolic and diastolic pressure measured in the brachial artery because there is practically negligible pressure pulse amplification between the brachial and the radial artery.

The subendocardial viability index, an indicator of myocardial workload and perfusion ($O_2$ supply vs. demand) was calculated as the ratio of the integral of diastolic pressure and time to the integral of systolic pressure and time. Low SEVR (Subendocardial viability ratio) has been shown to be associated with coronary artery disease, decreased coronary flow reserve in patients with healthy coronary arteries, severity of Type I and Type II diabetes, decreased renal function, and a history of smoking.

Assessment of Arterial Stiffness (baPWV, ABI)

Brachial-ankle pulse wave velocity (baPWV) is also used to evaluate arterial stiffness. Pulse wave velocity is the speed at which the blood pressure pulse travels from the heart to the peripheral artery after blood rushes out during contraction. It is mainly used to evaluate stiffness of the artery wall. Pulse wave velocity increases with stiffness of the arteries. The PTT (Pulse Transit Time) of each segment is calculated from the waveform taken from each sensor. Pulse wave velocity is defined in Equation (1):

$$PWV = \frac{L \text{ (distance)}}{PTT \text{ (Pulse Transit Time)}} \quad \text{Equation (1)}$$

This method calculates heart-brachial PWV of both upper limbs, heart-ankle PWV of both lower limbs, brachial-ankle PWV of both right and left limb pairs, and effective estimated carotid-femoral PWV is calculated. See Equations (2), (3), and (4):

$$ha\ PWV \text{ (heart ankle } PWV) = \frac{Lha}{PTTha} \quad \text{Equation (2)}$$

$$hb\ PWV \text{ (heart brachial } PWV) = \frac{Lhb}{PTThb} \quad \text{Equation (3)}$$

$$ba\ PWV \text{ (brachial ankle } PWV) = \frac{Lba}{PTTba} \quad \text{Equation (4)}$$

Where Lha=Distance between heart and respective ankle

Lhb=Distance between heart and respective brachium.

Lba=Distance between respective brachium and ankle

Brachial Ankle Pulse Wave Velocity (baPWV), Ankle Brachial Index (ABI) and Blood Pressure (BP) were measured using an automatic waveform analyzer (model BP-203 RPE; Colin Medical Technology, Komaki, Japan). Measurements were taken with patients lying in a supine position after 5 minutes of rest in that position. Occlusion and monitoring cuffs were placed snugly around both sites of the upper and lower extremities of patients. Pressure waveforms of the brachial and tibial arteries were then recorded simultaneously by an oscillometric method. Measurement of right and left baPWV was obtained for an average of 10 seconds. The average of left and right baPWV will be used for analysis.

Method for Recording of Cardiac Output (Lt/Min)

Recording of cardiac output (CO) was performed using L&T Nivomon monitor (Larsen & Toubro Ltd., Mumbai, India). Noninvasive continuous cardiac output monitor with peripheral blood flow measurement option. This equipment is very useful and versatile. It calculates many cardiac parameters directly including cardiac output. It works on the features of impedance plethysmography principle and has tetrapolar configuration. The advantage is that this equipment directly calculates the cardiac output along with other parameters using the pulse wave.

Study (b) part (i). Cold pressor test (CPT) is an experimental stress paradigm based on a short term painful stimulation by immersing the hand into ice-cold water. This paradigm has been frequently used in stress research and is known to be associated with substantial activation of the autonomic nervous system as well as mild to moderate activation of the hypothalamic pituitary adrenocortical (HPA) axis. CPT is known to cause a global sympathetic activation in subjects with different levels of baseline sympathetic tone, such as a group of normal subjects and patients with borderline hypertension. Sympathetic-mediated vasoconstriction induced by the CPT leads to acute increases in peripheral BP, aortic BP, and wave reflection in healthy subjects without increasing the heart rate. The CPT has been used to evaluate the efficacy of lifestyle and pharmacological interventions on BP and vascular reactivity.

The cold pressor test is typically performed by immersing a subject's hand into ice water for a short period of time and is a potent stimulus for eliciting large elevations in blood pressure. The subject was asked to immerse his non-dominant hand till the wrist in the water bath maintained at 35° C. for hand again in water bath maintained at 35° C. for 1 minute for normalization of temperature. Results are presented in Table VI.

Study (b) part (ii). Mental Stress Test is a mental arithmetic test is a validated and widely accepted test which can induce a considerable degree of perceived stress. In the present model of mental stress test, participants were instructed to perform psychomotor performance tests like choice discrimination test, digit symbol substitution test, digit vigilance task continuously and as quickly and as accurately as possible for three times, instead of arithmetic test. The total duration of the mental stress test was 5 min. During the test, a metronome was played loudly with headphones as a distracter. This also acted as source of mental or psychological stress. Results are presented in Table VII.

TABLE VI

Effect of Capros ® on cold pressor induced changes in waveform reflections (n = 06)

Data are expressed as the mean ± SD

| | Capros | | | | Placebo | | | |
| --- | --- | --- | --- | --- | --- | --- | --- | --- |
| | Pretreatment | | Post Treatment | | Pretreatment | | Post Treatment | |
| | Baseline | within 2 min. of hand immersion | Baseline | within 2 min. of hand immersion | Baseline | within 2 min. of hand immersion | Baseline | within 2 min. of hand immersion |
| HR (bpm) | 65.6 ± 5.93 | 68.3 ± 7.92 | 65.53 ± 3.52 | 69.1 ± 7.27 | 68.4 ± 2.82 | 66.5 ± 5.12 | 66.9 ± 2.13 | 68.7 ± 7.80 |
| AAP (mmHg) | 2.40 ± 4.64 | 2.8 ± 6.10 | 1.1 ± 4.69 | 2.30 ± 4.41 | 3.0 ± 3.39 | 3.80 ± 2.38 | 3.60 ± 2.70 | 5.10 ± 2.34 |
| AIx (%) | 112.6 ± 23.63 | 114 ± 26.12 | 106.6 ± 19.19 | 105.8 ± 19.52 | 111 ± 20.62 | 119.4 ± 17.68 | 112.6 ± 19.30 | 117.4 ± 18.47 |
| SEVR (%) | 154.73 ± 23.29 | 142.33 ± 11.86 | 152.8 ± 20.60 | 158.5 ± 14.16 | 156.93 ± 19.61 | 147.73 ± 16.78 | 152.9 ± 20.60 | 149.7 ± 18 |
| SP | 113.6 ± 3.36 | 127 ± 1.87 | 112.2 ± 2.17 | 120.6 ± 2.61 | 112.8 ± 2.28 | 122.8 ± 5.17 | 115.6 ± 3.85 | 125 ± 5.10 |
| DP | 70 ± 5.96 | 76.4 ± 7.44 | 70.2 ± 5.4 | 73.2 ± 8.23 | 69 ± 2.24 | 72.6 ± 2.14 | 72 ± 3.16 | 78.4 ± 2.70 |
| MP | 84.6 ± 7.54 | 92.8 ± 6.88 | 83.37 ± 4.81 | 88.8 ± 9.4 | 83.2 ± 1.92 | 89 ± 6.75 | 83.36 ± 4.81 | 88.8 ± 9.40 |
| PP | 43.6 ± 2.97 | 50.6 ± 8.96 | 42 ± 6.52 | 49.2 ± 6.87 | 43.8 ± 2.86 | 50 ± 9.17 | 42 ± 6.52 | 49.2 ± 6.87 |
| SP | 99.1 ± 8.66 | 109.8 ± 7.36 | 97.63 ± 4.39 | 104.8 ± 9.24 | 96.9 ± 3.87 | 104.4 ± 5.18 | 98.4 ± 4.56 | 110.8 ± 2.28 |
| DP | 70.9 ± 6.09 | 77.5 ± 7.43 | 71.1 ± 5.59 | 74.1 ± 8.29 | 71.2 ± 7.69 | 74.4 ± 9.40 | 75.2 ± 4.76 | 79.9 ± 3.81 |
| MP | 84.6 ± 7.54 | 92.8 ± 6.88 | 83.37 ± 4.81 | 88.8 ± 9.4 | 78.4 ± 5.50 | 83.8 ± 9.98 | 83.3 ± 4.81 | 88.9 ± 5 |
| PP | 28.2 ± 4.34 | 32.3 ± 3.17 | 26.53 ± 4.83 | 31.7 ± 6.15 | 26.2 ± 5.45 | 29.4 ± 5.59 | 26.5 ± 4.83 | 31.7 ± 6.15 |

AP: Aortic Pressure

AIx: Augmentation index

SEVR: Subendocardial viability ratio 120 seconds, and at the end of this period, pressure of 20 mm less than the normal diastolic pressure of the individual is applied using BP cuff on the lower part of his non-dominant hand. Immediately after applying the pressure the subject was asked to immerse his non-dominant hand till the wrist in to the cold water bath maintained at 4-5° C. (for about 1 min) until he was able to sense what was perceived to be unbearable pain, or up to a certain reasonable threshold. The subjects were instructed to remain relaxed, breathe normally, during hand immersion. The subject was then asked immerse his As shown above in Table VI, the results from the cold pressor study are presented. Compared to baseline and placebo treatment, Capros produced a statistically significant decrease in aortic pressure and augmentation index. Further, both radial and aortic pressures also decreased significantly. An increase in SEVR was also significant. This indicates that Capros®, by decreasing the augmentation index (which indicates decreased wave reflections from the periphery and/or delayed return of the reflected wave), may lead to decreased arterial stiffness.

TABLE VII

Effect of Capros ® on mental stress induced changes in waveform reflections (n = 06)
Data are expressed as the mean ± SD

|  | Capros | | | | Placebo | | | |
|---|---|---|---|---|---|---|---|---|
|  | Pretreatment | | Post Treatment | | Pretreatment | | Post Treatment | |
|  | Baseline | within 2 min. of stress test | Baseline | within 2 min. of stress test | Baseline | within 2 min. of stress test | Baseline | within 2 min. of stress test |
| HR (bpm) | 66.1 ± 4.16 | 66.7 ± 2.84 | 65.53 ± 3.52 | 66 ± 2.62 | 68.4 ± 2.82 | 66.5 ± 5.12 | 66.9 ± 2.13 | 70.7 ± 5.35 |
| AP (mmHg) | 2.4 ± 3.85 | 5.1 ± 4.59 | 1.3 ± 4.60 | 3.4 ± 5.56 | 3 ± 2.92 | 5.2 ± 3.83 | 3.6 ± 3.29 | 5.8 ± 4.21 |
| AIx (%) | 110.8 ± 20 | 119.4 ± 24.27 | 106.6 ± 19.19 | 114 ± 22.39 | 109.2 ± 19.64 | 121.2 ± 19.52 | 110 ± 20.25 | 120.8 ± 22.84 |
| SEVR (%) | 152.3 ± 22.58 | 144.5 ± 6.80 | 162.8 ± 14.34 | 157 ± 11.60 | 156.93 ± 19.61 | 149.43 ± 19.67 | 152.92 ± 20.60 | 150.0 ± 17.56 |
| SP | 113.4 ± 3.05 | 115.6 ± 4.39 | 112.2 ± 2.17 | 114.2 ± 7.66 | 112.8 ± 2.28 | 117.8 ± 2.68 | 115.6 ± 3.85 | 120.8 ± 3.03 |
| DP | 70.4 ± 6.66 | 71 ± 7.49 | 70.2 ± 5.40 | 71.6 ± 7.27 | 70 ± 3.16 | 73.8 ± 3.03 | 72.4 ± 3.58 | 77.2 ± 3.35 |
| MP | 84.3 ± 6.69 | 86.8 ± 7.93 | 83.36 ± 4.80 | 85.5 ± 8.65 | 84.2 ± 2.69 | 88.4 ± 2.70 | 86.8 ± 2.64 | 91.7 ± 1.67 |
| PP | 43 ± 5.70 | 44.6 ± 5.55 | 42 ± 6.52 | 42.6 ± 8.26 | 42.8 ± 2.28 | 44 ± 2.35 | 43.2 ± 5.40 | 43.6 ± 5.90 |
| SP | 98.2 ± 6.53 | 102 ± 8.19 | 97.63 ± 4.39 | 100.9 ± 11.18 | 96.1 ± 6.07 | 100.8 ± 5.76 | 98.8 ± 4.15 | 103.3 ± 5.09 |
| DP | 71.4 ± 6.66 | 72.2 ± 7.79 | 71.1 ± 5.59 | 72.5 ± 7.47 | 71.2 ± 5.76 | 72.8 ± 5.63 | 72.4 ± 4.77 | 74.4 ± 4.34 |
| MP | 84.3 ± 6.69 | 86.8 ± 7.93 | 83.36 ± 4.80 | 85.5 ± 8.65 | 79.5 ± 5 | 82.1 ± 4.58 | 81.2 ± 4.46 | 84. ± 4.34 |
| PP | 26.8 ± 2.17 | 29.8 ± 2.75 | 26.53 ± 4.83 | 28.4 ± 7.25 | 24.9 ± 6.50 | 28 ± 7.11 | 26.4 ± 2.19 | 28.9 ± 3.25 |

AAP: Aortic Pressure
AIx: Augmentation index
SEVR: Subendocardial viability ratio As shown above in Table VII, the results from the mental stress test study are presented. There was no significant difference in the baseline hemodynamic values between the two treatment groups. Compared to baseline and placebo, a significant decline in aortic pressure was observed with Capros®. Similarly a decrease in augmentation index and SEVR were observed, which were, however, not statistically significant. Both radial and aortic systolic pressures showed a decrease which was insignificant. However, no change can be seen with diastolic blood pressure. These observations indicate that Capros®, by decreasing the augmentation index (as indicated by decreased wave reflections from the periphery and/or delayed return of the reflected wave), may lead to decreased arterial stiffness.

Another larger study (c) was performed. The study was a prospective, randomized, double blind trial conducted in the Department of Clinical Pharmacology and Therapeutics, Nizam's Institute of Medical Sciences, Hyderabad, India. Forty two patients were enrolled in the study which was approved by the Institutional Ethics Committee. All subjects gave written informed consent prior to participation in the study.

Study (c) design. Patients of either sex, aged 18-75 years, fasting plasma glucose of ≥110 mg/dL, a glycosylated haemoglobin (HbA1c) between 7% and 9% and taking stable dose of anti-diabetic treatment (Metformin 1500-2500 mg/day) for the past 8 weeks prior to the screening visit; and having endothelial dysfunction defined as ≤6% change in reflection index (RI) on post salbutamol challenge test, were included in the study. Patients with severe uncontrolled hyperglyceamia, uncontrolled hypertension, cardiac arrhythmia, impaired hepatic or renal function, history of malignancy or stroke, smoking, chronic alcoholism, any other serious disease requiring active treatment and treatment with any other herbal supplements, were excluded from the study.

After screening, all the eligible subjects were randomized to receive either one of the four treatments for a duration of 12 weeks, as follows. Group 1: one capsule of CAPROS® 250 mg twice daily, group 2: one capsule of CAPROS® 500 mg twice daily; group 3: one capsule of Placebo in morning or one capsule of Atorvastatin 10 mg in evening daily; and group 4: only Placebo twice daily.

Subjects were reviewed for follow up at 4 weeks, 8 and 12 weeks of therapy. At each visit they were evaluated for efficacy and safety. Pharmacodynamic evaluation for endothelial function was conducted at every visit. A blood sample was collected for evaluation of biomarkers before and at the end of treatment. Inhibition of platelet aggregation was also studied with as indicated below. Safety lab investigations for hematological, hepatic and renal biochemical parameters were conducted before and at the end of the study, and also as and when required (in case of any adverse drug reaction (ADR)). Subjects were interviewed for the presence of ADRs and the same was recorded in the case report form (CRF). Compliance to therapy was assessed by pill count method.

The clinical measurements and pharmacodynamic tests were performed as described above in studies (a) or (b), unless otherwise stated.

Biomarker Evaluation.

Nitric oxide, MDA, Glutathione (GSH) and levels thereof were estimated spectrophotometrically as described above, and HsCRP (high sensitivity C-reactive protein) by ELISA method.

Safety Assessments.

All the subjects had undergone complete physical examination, safety lab evaluations at baseline and at the end of the treatment. Samples were collected after an overnight fast of 12 hrs after the last dose of medication for determination of haemoglobin, HbA1c, blood urea and serum creatinine, liver function test, and lipid profile (Total cholesterol (TC), High density lipoprotein cholesterol (HDL-C), low density lipoprotein cholesterol (LDL-C)), and results obtained using appropriate standard techniques.

There were no significant changes in hematological, renal and hepatic functions observed with any of the treatments. All subjects tolerated therapy well. There were no serious adverse events recorded in the study.

Primary and Secondary Efficacy Parameters.

The primary efficacy measure was a change in endothelial dysfunction as assessed by more than 6% change in reflection index (RI) at 12 weeks in all the treatment groups. Secondary efficacy parameters include change in oxidative stress markers, serum levels of nitric oxide at 12 weeks in all the treatment groups. Additionally, safety and tolerability assessment of the test medications were also conducted.

Data Analysis.

Data are expressed as mean±SD. ANOVA and paired and unpaired t-test were performed for within group and between groups analysis respectively. A p-value <0.05 was considered to be statistically significant. All statistical analyses were performed using the Prism Graphpad 4 (GraphPad Software, Inc., La Jolla, Calif., USA).

Results of Study (c). Study (c) is an extension of study (a).

A total of 88 Type 2 Diabetic Subjects: subjects were screened and 80 eligible subjects completed the study. Twenty subjects each in CAPROS® 250 mg, CAPROS® 500 mg, Atorvastatin 10 mg and Placebo groups completed the study.

TABLE VIII

Demographic characteristics of all study groups

| Parameter | CAPROS ®250 mg | CAPROS ®500 mg | Atorvastatin | Placebo |
|---|---|---|---|---|
| Total No | 20 | 20 | 20 | 20 |
| Age in Yrs | 57.60 ± 9.67 | 57.75 ± 9.86 | 56.95 ± 8.04 | 56.90 ± 9.17 |
| Gender (M/F) | 13/7 | 15/5 | 13/7 | 12/8 |
| Bodyweight (Kg) | 69.3 ± 11.19 | 65.87 ± 7.31 | 68.56 ± 8.47 | 67.42 ± 6.75 |
| BMI (Kg/m$^2$) | 24.88 ± 2.76 | 25.22 ± 2.67 | 26.02 ± 3.12 | 24.75 ± 2.41 |

Detailed demographic characteristics of the four study groups are shown in Table VIII. There were no significant differences between treatment groups in baseline characteristics including age, weight and body mass index.

TABLE IX

Type 2 Diabetic Subjects: Effect of CAPROS250 ®, CAPROS 500 ®, Atorvastatin 10 mg & Placebo on marker of endothelial function (RI %)

| | CAPROS250 ® (n = 20) | | CAPROS 500 ® (n = 20) | | Atorvastatin (n = 20) | | Placebo (n = 20) | |
|---|---|---|---|---|---|---|---|---|
| RI(%) | Pre TT A | Post TT B | Pre TT C | Post TT D | Pre TT E | Post TT F | Pre TT G | Post TT H |
| Mean | −2.25 | −9.13$ | −2.11 | −10.04$ | −2.68 | −11.03$ | −2.32 | −0.90 |
| SD | ±1.37 | ±2.56 | ±0.98 | ±0.92 | ±1.13 | ±3.93 | ±1.21 | ±2.83 |

Baseline RI nonsignificant between all four treatments (A & C, A & E, A & G, C & E, C & G, E & G)
$p < 0.001 when compared between B & A, D & C, F & E, H & B, H & D, H & F
Nonsignificant when compared between D & B, D & F, B & F

TABLE X

Type 2 Diabetic Subjects: Effect of CAPROS250 ®, CAPROS 500 ®, Atorvastatin 10 mg & Placebo on other Cardiovascular pharmacodynamic parameters

| Parameter | CAPROS250 ® (n = 20) | | CAPROS 500 ® (n = 20) | | Atorvastatin (n = 20) | | Placebo (n = 20) | |
|---|---|---|---|---|---|---|---|---|
| | Pre TT A | Post TT B | Pre TT C | Post TT D | Pre TT E | Post TT F | Pre TT G | Post TT H |
| AIx (%) | 134.4 ± 12.6 | 132.4 ± 11.45# | 137.0 ± 14.41 | 127.7 ± 12.31$ | 135.5 ± 14.71 | 123.4 ± 13.4$ | 134.4 ± 17.21 | 135.5 ± 16.17 |
| SEVR (%) | 138.7 ± 11.5 | 140.4 ± 11.48# | 135.7 ± 13.79 | 145.7 ± 18.90$ | 135.4 ± 19.11 | 146.5 ± 16.09$ | 131.8 ± 11.08 | 129.9 ± 11.75 |
| ABI | 1.05 ± 0.06 | 1.08 ± 0.04 NS | 1.05 ± 0.11 | 1.11 ± 0.08$ | 1.02 ± 0.07 | 1.10 ± 0.04$ | 1.07 ± 0.08 | 1.04 ± 0.06 |
| PWV cm/s | 1498 ± 143.7 | 1436 ± 198.3# | 1528 ± 212.3 | 1360 ± 198.2$ | 1522 ± 127.7 | 1346 ± 147.6$ | 1555 ± 117.5 | 1571 ± 114.5 |
| CO lt/min | 4.21 ± 0.62 | 4.53 ± 0.69# | 4.60 ± 1.05 | 5.12 ± 1.39* | 4.13 ± 0.65 | 5.15 ± 0.47$ | 4.44 ± 0.64 | 4.37 ± 0.60 |
| SVR (dyne · sec/cm$^5$) | 1528 ± 362.4 | 1447 ± 268.3NS | 1509 ± 364.2 | 1363 ± 293.4* | 1519.25 ± 296.3 | 1336.95 ± 251.3$ | 1518 ± 295.5 | 1540 ± 290.4 |

Baseline values for all treatments are comparable
AIx - #p < 0.05 compared between B & A, $p < 0.001between D & C, F & E
SEVR - #p < 0.05 compared between B & A, $p < 0.001between D & C, F & E
ABI - Nonsignificant (NS) compared between B & A, $p < 0.001between D & C, F & E
PWV - #p < 0.05 compared between B & A, $p < 0.001between D & C, F & E
CO - #p < 0.05 compared between B & A, *p < 0.01 between D & C, $p < 0.001between F & E7. SVR (Systemic Vascular Resistance) - Nonsignificant (NS) compared between B& A, *p < 0.01 between D & C, $p < 0.001 compared between F & E In placebo group nonsignificant for all parameters compared between H & G

TABLE X-A

Type 2 Diabetic Subjects: Comparison of Absolute change in the Pharmacodynamic parameters

| Parameter | CAPROS250 ® (n = 20) A | CAPROS 500 ® (n = 20) B | Atorvastatin (n = 20) C | Placebo (n = 20) D |
|---|---|---|---|---|
| RI (%) | −6.88 ± 2.71 | −7.93 ± 1.35 | −8.35 ± 4.17 | 1.42 ± 3.15 |
| AIx (%) | −1.95 ± 3.61 | −9.32 ± 6.25 | −12.14 ± 5.44 | 1.10 ± 3.16 |
| SEVR (%) | 1.67 ± 2.83 | 10.02 ± 9.78 | 11.09 ± 6.51 | −1.85 ± 4.59 |
| ABI | 0.03 ± 0.07 | 0.07 ± 0.071 | 0.08 ± 0.06 | −0.02 ± 0.07 |
| PWV (cm/s) | −61.25 ± 111.35 | −168.25 ± 109.91 | −175.5 ± 110.82 | 16.00 ± 58.50 |
| CO lt/min | 0.32 ± 0.57 | 0.52 ± 0.67 | 0.84 ± 0.43 | −0.07 ± 0.19 |
| SVR (dyne · sec/cm$^5$) | −81 ± 204.62 | −145.35 ± 205.44 | −182.3 ± 109.61 | 21.90 ± 145.30 |

All values expressed as Mean ± SD
RI index- Non-significant when compared between A & B, A & C, B & C
$p < 0.001$ when compared between A & D, B & D, C & D. (See, FIG. 1.)
AIx- $p < 0.001$ compared between B & A, A & C, Nonsignificant when compared between B & C,
$p < 0.01$ between A & D, $p < 0.001$ between B & D, C & D
SEVR-$p < 0.001$ when compared between A & B, A & C and Nonsignificant between B & C
$p < 0.01$ when compared between A & D, B & D and $p < 0.001$ compared between C & D
ABI- Nonsignificant compared between A & B, B & C, $p < 0.05$ compared between C & A
$p < 0.05$ when compared between A & D, $p < 0.001$ between B & D and between C & D
PWV- $p < 0.01$ compared between A & B, A & C and Nonsignificant between B & C
$p < 0.01$ when compared between A & D, $p < 0.001$ between B & D and C & D
CO- Nonsignificant when compared between A & B and B & C, $p < 0.01$ between A & C
$p < 0.01$ compared between A & D, $p < 0.001$ compared between B & D and C & D
SVR- Nonsignificant when compared between A & B, B & C and between A & C, A & D
$p < 0.01$ when compared between B & D, $p < 0.001$ when compared between C & D The above Table X-A includes results that pertain to FIG. 1 which shows that after 12 weeks of treatment, an extract of *Phyllanthus emblica* was effective to significantly reduce reflection index (RI) in a patient suffering from type 2 DM. The observed improvement in RI was comparable to that observed for patients receiving atorvastatin.

TABLE XI

Type 2 Diabetic Subjects: Effect of CAPROS250 ®, CAPROS 500 ®, Atorvastatin 10 mg & Placebo on Biomarkers of Oxidative Stress

| Parameter | CAPROS250 ® (n = 20) | | CAPROS 500 ® (n = 20) | | Atorvastatin (n = 20) | | Placebo (n = 20) | |
|---|---|---|---|---|---|---|---|---|
| | PreTT A | Post TT B | PreTT C | Post TT D | PreTT E | Post TT F | PreTT G | Post TT H |
| NO (µM/L) | 32.02 ± 14.81 | 43.31 ± 16.99 | 33.27 ± 11.07 | 49.03 ± 11.22 | 35.24 ± 9.71 | 63.69 ± 15.04 | 39.29 ± 8.15 | 37.88 ± 9.22 |
| MDA (nM/ml) | 3.23 ± 1.34 | 2.35 ± 1.00 | 3.35 ± 1.00 | 2.29 ± 0.78 | 3.54 ± 0.85 | 2.37 ± 0.59 | 3.47 ± 0.65 | 3.56 ± 0.52 |
| GSH (µM/L) | 437.71 ± 143.2 | 560.2 ± 169.4 | 405.7 ± 107.1 | 626.7 ± 143.1 | 418.8 ± 166.7 | 641.8 ± 150.2 | 431.8 ± 136.1 | 435.9 ± 128.1 |
| hsCRP (Mg/L) | 2.91 ± 1.53 | 1.59 ± 0.98 | 3.50 ± 1.05 | 1.25 ± 0.42 | 3.08 ± 1.38 | 0.97 ± 0.78 | 3.09 ± 1.44 | 2.94 ± 1.47 |

Baseline values between all treatments are comparable
NO - $p < 0.001$ when compared between B & A, D & C and F & E
GSH - $p < 0.001$ when compared between B & A, D & C and F & E
MDA - $p < 0.001$ when compared between B & A, D & C and F & E
hsCRP - $p < 0.001$ when compared between B & A, D & C and F & E
In placebo group nonsignificant for all biomarkers between when compared between G & H

TABLE XI-A

Type 2 Diabetic Subjects: Mean percentage change in Biomarkers of Oxidative stress after 12 weeks treatment with CAPROS ® 250 mg, CAPROS ® 500 mg, Atorvastatin 10 mg and Placebo

| Parameter | CAPROS ® 250 mg (n = 20) A | CAPROS ® 500 mg (n = 20) B | Atorvastatin (n = 20) C | Placebo (n = 20) D |
|---|---|---|---|---|
| NO (µM/L) | 43.13 ± 38.44 | 54.60 ± 32.28 | 88.44 ± 50.97 | −3.70 ± 10.81 |
| MDA (nM/ml) | −23.84 ± 22.47 | −28.60 ± 22.89 | −30.55 ± 19.81 | 3.76 ± 10.24 |
| GSH (µM/L) | 30.34 ± 22.06 | 61.55 ± 43.57 | 68.40 ± 58.76 | 1.87 ± 5.87 |
| hsCRP (Mg/L) | −44.56 ± 22.97 | −63.16 ± 9.76 | −64.90 ± 26.99 | −5.08 ± 21.53 |

Figure 2:
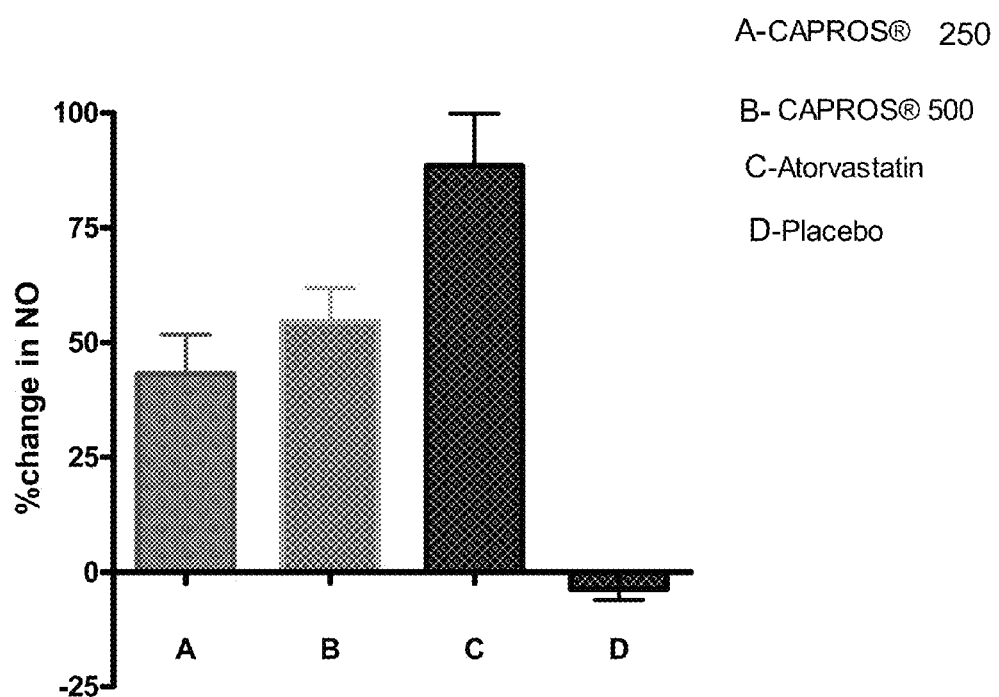
FIG. 2 illustrates mean percent change in nitric oxide (NO) concentration level in type 2 diabetic individuals before and after 12 weeks treatment in one embodiment in accordance with the present invention with an extract of *Phyllanthus emblica*, or atorvastatin, as described in Table XI-A.
Figure 3:
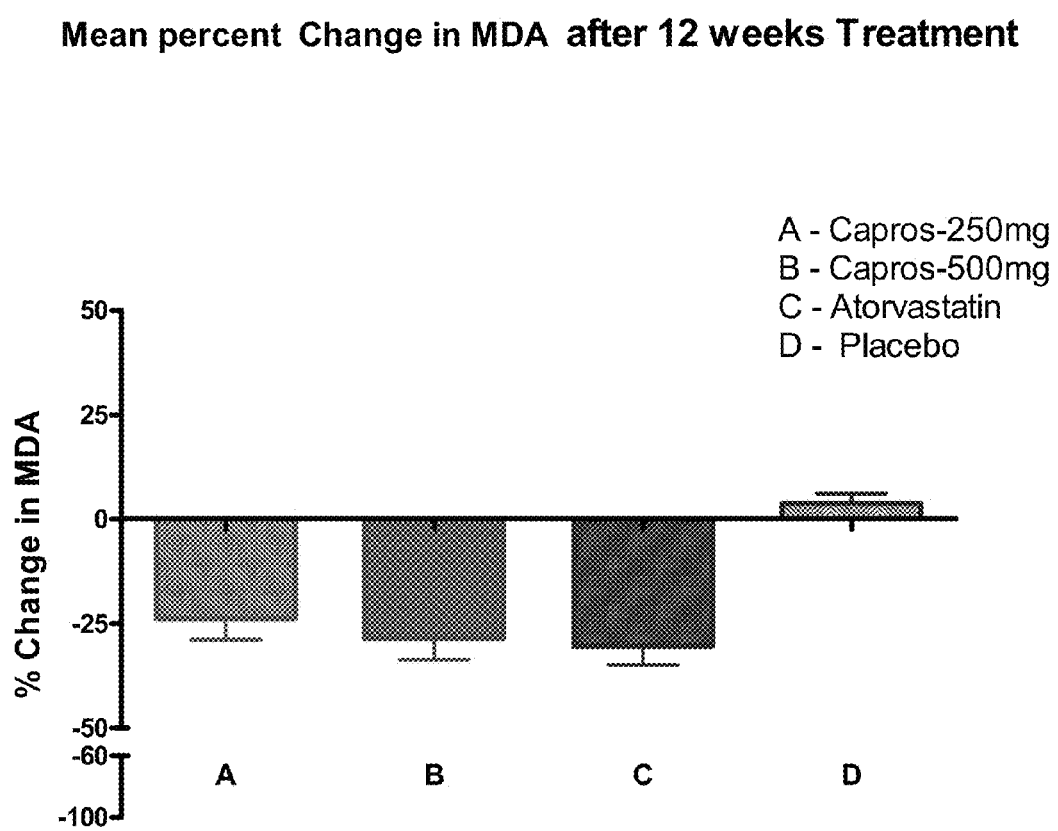
FIG. 3 illustrates mean percent change in malondialdehyde (MDA) concentration level in type 2 diabetic individuals before and after 12 weeks treatment in one embodiment in accordance with the present invention with an extract of *Phyllanthus emblica*, or atorvastatin, as described in Table XI-A.
Figure 4:
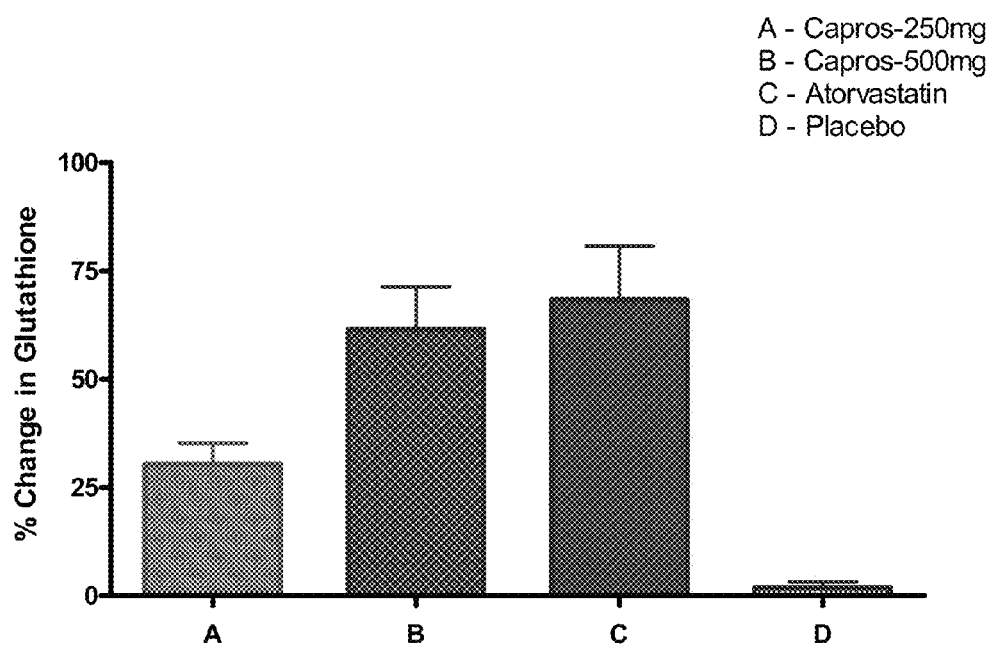
FIG. 4 illustrates mean percent change in glutathione (GSH) concentration level in type 2 diabetic individuals before and after 12 weeks treatment in one embodiment in accordance with the present invention with an extract of *Phyllanthus emblica*, or atorvastatin, as described in Table XI-A.
Figure 5:
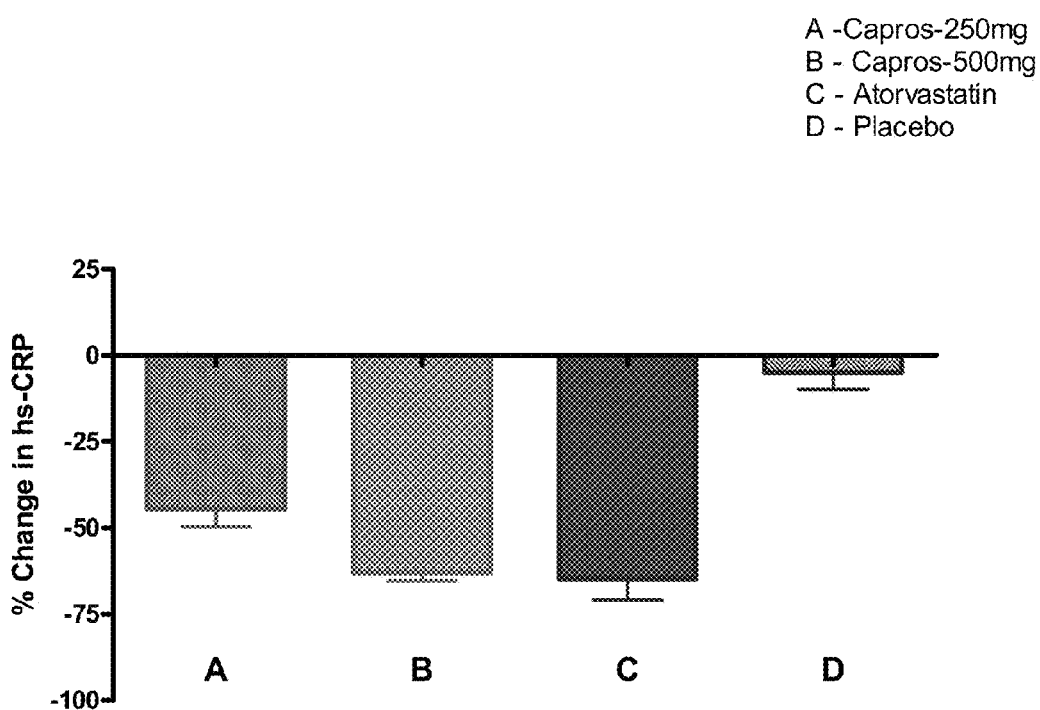
FIG. 5 illustrates mean percent change in high sensitivity C-reactive protein (hs-CRP) concentration level in type 2 diabetic individuals before and after 12 weeks treatment in one embodiment in accordance with the present invention with an extract of *Phyllanthus emblica*, or atorvastatin, as described in Table XI-A.

NO- Nonsignificant when compared between A & B, $p < 0.005$ B & C
$p < 0.01$ between A & C and $p < 0.001$ between A & D, B & D and C & D. (See, FIG. 2.)
MDA-Nonsignificant when compared between A & B, B & C and A & C
$p < 0.001$ when compared between A & D, B & D and C & D. (See, FIG. 3.)
GSH-$p < 0.01$ when compared between A & B and A & C, Nonsignificant between B & C
$p < 0.001$ when compared between A & B, B & D and C & D. (See, FIG. 4.)
hsCRP-$p < 0.01$ when compared between A & B, Nonsignificant between B & C, $p < 0.05$ between A & C
$p < 0.001$ when compared between A & D, B & D and C & D. (See, FIG. 5.)

The above Table XI-A includes results that pertain to FIGS. 2-5 which show that after 12 weeks of treatment, an extract of *Phyllanthus emblica* was effective to significantly improve certain levels of biomarkers in a patient suffering from type 2 DM. In particular, levels of NO and glutathione were observed to increase significantly in a dose dependent manner, while levels of MDA and hs-CRP were observed to decrease significantly in a dose dependent manner. The observed improvement in these biomarkers was comparable to that observed for patients receiving atorvastatin.

TABLE XI-B

Type 2 Diabetic Subjects: Comparison of Absolute change in Biomarkers between the four treatment groups -

| Parameter | CAPROS250 ® (n = 20) A | CAPROS 500 ® (n = 20) B | Atorvastatin (n = 20) C | Placebo (n = 20) D |
|---|---|---|---|---|
| NO (μM/L) | 11.29 ± 9.82 | 15.76 ± 6.85 | 28.45 ± 12.30 | −1.41 ± 4.08 |
| MDA (nM/ml) | −0.87 ± 0.82 | −1.06 ± 0.88 | −1.17 ± 0.75 | 0.09 ± 0.29 |
| GSH (μM/L) | 122.45 ± 87.12 | 221.06 ± 108.87 | 222.99 ± 140.15 | 4.02 ± 18.21 |
| hsCRP (Mg/L) | −1.33 ± 1.00 | −2.26 ± 0.81 | −2.10 ± 1.26 | −0.15 ± 0.52 |

All values expressed as Mean ± SD

NO-Nonsignificant when compared between A & B, $p < 0.001$ between B & C and A & C $p < 0.001$ between A & D, B & D and A & D MDA- Nonsignificant between A & B, B & C and A & C $p < 0.001$ when compared between A & D, B & D and A & D GSH- $p < 0.01$ when compared between A & B, A & C and Nonsignificant between B & C $p < 0.001$ when compared between A & D, B & D and C & D hsCRP -$p < 0.01$ when compared between A & B and $p < 0.05$ between A & C Nonsignificant when compared between B & C $p < 0.001$ when compared between A & D, B & D, between C & D

TABLE XII

Type 2 Diabetic Subjects: Effect of CAPROS ® 250 mg, CAPROS ® 500 mg, Atorvastatin 10 mg and Placebo on Lipid profile

| Parameter | CAPROS ® 250 mg (n = 20) PreTT A | CAPROS ® 250 mg (n = 20) Post TT B | CAPROS ® 500 mg (n = 20) Pre TT C | CAPROS ® 500 mg (n = 20) Post TT D | Atorvastatin (n = 20) PreTT E | Atorvastatin (n = 20) Post TT F | Placebo (n = 20) PreTT G | Placebo (n = 20) Post TT H |
|---|---|---|---|---|---|---|---|---|
| Total Cholesterol (mg/dl) | 183.7 ± 30.04 | 161.8 ± 19.81 | 193.2 ± 24.90 | 164.5 ± 22.53 | 183.7 ± 37.41 | 135.6 ± 26.94 | 188.9 ± 35.20 | 192.2 ± 32.73 |
| HDL-C (mg/dl) | 39.10 ± 4.12 | 42.10 ± 5.58 | 41.45 ± 6.73 | 47.70 ± 6.17 | 40.44 ± 6.76 | 47.95 ± 5.34 | 38.35 ± 5.21 | 37.50 ± 5.68 |
| LDL-C (mg/dl) | 116.9 ± 28.24 | 95.90 ± 19.43 | 124.3 ± 27.49 | 92.60 ± 25.35 | 126.00 ± 34.90 | 78.50 ± 16.71 | 126.2 ± 39.45 | 135.5 ± 45.27 |
| Triglycerides (mg/dl) | 150.8 ± 42.50 | 132.0 ± 39.82 | 164.5 ± 70.54 | 123.8 ± 41.52 | 155.0 ± 56.51 | 106.5 ± 30.79 | 164.3 ± 21.70 | 169.0 ± 19.85 |
| VLDL-C (mg/dl) | 27.25 ± 7.12 | 24.20 ± 5.86 | 31.35 ± 10.58 | 24.45 ± 5.73 | 25.20 ± 6.57 | 19.90 ± 3.64 | 26.40 ± 5.17 | 25.6 ± 4.98 |

Baseline values between all treatments are comparable

TC - $p < 0.001$ when compared between B & A, D & C and between F & E

HDL-C - $p < 0.01$ when compared between B & A, D & C, $p < 0.001$ between F & E LDL-C - $p < 0.01$ when compared between B & A, D & C and $p < 0.001$ F & E TG $p < 0.01$ when compared between B & A, $p < 0.001$ between D & C and F & E VLDL-C - $p < 0.01$ when compared between B & A, D & C and $p < 0.001$ between F & E In placebo group nonsignificant for all parameters compared between H & G

TABLE XII-A

Type 2 Diabetic Subjects: Comparison of Absolute change in Lipid profile between the four treatments

| Parameter | CAPROS ® 250 mg (n = 20) A | CAPROS ® 500 mg (n = 20) B | Atorvastatin (n = 20) C | Placebo (n = 20) D |
|---|---|---|---|---|
| Total Cholesterol (mg/dl) | −21.90 ± 24.53 | −28.7 ± 23.21 | −48.11 ± 36.87 | 3.30 ± 38.41 |
| HDL-C (mg/dl) | 3.00 ± 4.34 | 6.25 ± 7.68 | 7.52 ± 7.00 | −0.85 ± 2.54 |
| LDL-C (mg/dl) | −21.00 ± 25.26 | −31.65 ± 36.73 | −47.48 ± 24.19 | 9.30 ± 57.52 |

TABLE XII-A-continued

Type 2 Diabetic Subjects: Comparison of Absolute change in Lipid profile between the four treatments

| Parameter | CAPROS ® 250 mg (n = 20) A | CAPROS ® 500 mg (n = 20) B | Atorvastatin (n = 20) C | Placebo (n = 20) D |
|---|---|---|---|---|
| Triglycerides (mg/dl) | −18.80 ± 21.71 | −40.65 ± 36.37 | −48.54 ± 50.09 | 4.70 ± 10.11 |
| VLDL-C (mg/dl) | −3.05 ± 4.19 | −6.90 ± 8.07 | −5.30 ± 4.70 | −0.75 ± 2.22 |

All values expressed as Mean ± SD
TC- nonsignificant when compared between A & B, between B & C, $p < 0.05$ between A & C
$p < 0.05$ when compared between A & D, $p < 0.01$ between B & D and $p < 0.001$ C & D
HDL-Nonsignificant between A & B, B & C and $p < 0.05$ between A & C
$p < 0.01$ when compared between A & D, $p < 0.01$ between B & D and $p < 0.001$ between C & D
LDL-C-Nonsignificant when compared between A & B, B & C and $p < 0.01$ between A & C
$p < 0.05$ when compared between A & D, B & D and $p < 0.001$ between C & D
TG - $p < 0.05$ when compared between A & B, Nonsignificant between B & C, $p < 0.05$ between A & C
$p < 0.001$ when compared between A & D, B & D and between C & D
VLDL-C-Nonsignificant when compared between A & B, B & C, A & C
$p < 0.05$ when compared between A & D, $p < 0.01$ between B & D and $p < 0.001$ between C & D

TABLE XII-B

Type 2 Diabetic Subjects: Mean percentage change in Lipid profile after 12 weeks treatment with CAPROS ® 250 mg, CAPROS ® 500 mg, Atorvastatin 10 mg and Placebo

| Parameter | CAPROS ® 250 mg (n = 20) A | CAPROS ® 500 mg (n = 20) B | Atorvastatin (n = 20) C | Placebo (n = 20) D |
|---|---|---|---|---|
| Total Cholesterol (mg/dl) | −10.89 ± 11.13 | −14.30 ± 11.12 | −24.68 ± 14.38 | 4.36 ± 22.36 |
| HDL-C (mg/dl) | 7.88 ± 10.95 | 17.75 ± 22.73 | 21.16 ± 20.49 | −2.20 ± 6.67 |
| LDL-C (mg/dl) | −15.88 ± 17.73 | −20.15 ± 37.44 | −35.00 ± 14.34 | 15.38 ± 47.29 |
| Triglycerides (mg/dl) | −11.15 ± 13.34 | −18.72 ± 20.26 | −25.02 ± 25.34 | 3.21 ± 6.56 |
| VLDL-C (mg/dl) | −9.94 ± 12.20 | −15.29 ± 25.79 | −18.24 ± 17.10 | −2.41 ± 8.87 |

Figure 6:
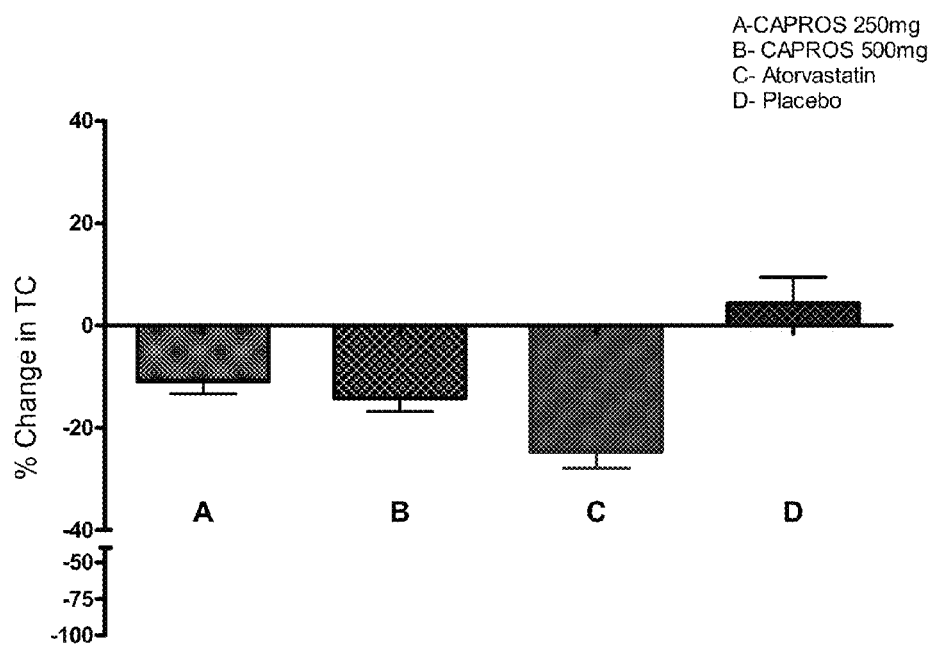
FIG. 6 illustrates mean percent change in total cholesterol (TC) concentration level in type 2 diabetic individuals before and after 12 weeks treatment in one embodiment in accordance with the present invention with an extract of *Phyllanthus emblica*, or atorvastatin, as described in Table XII-B.
Figure 7:
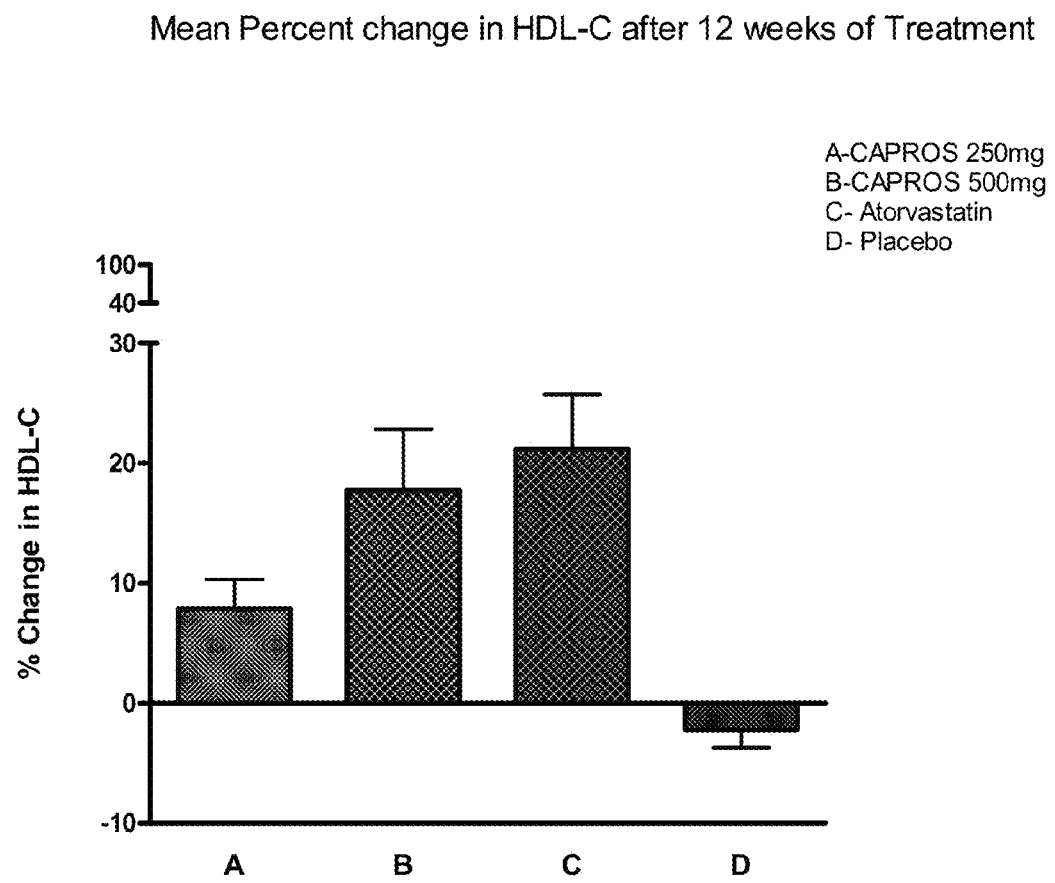
FIG. 7 illustrates mean percent change in HDL-C concentration level in type 2 diabetic individuals before and after 12 weeks treatment in one embodiment in accordance with the present invention with an extract of *Phyllanthus emblica*, or atorvastatin, as described in Table XII-B.
Figure 8:
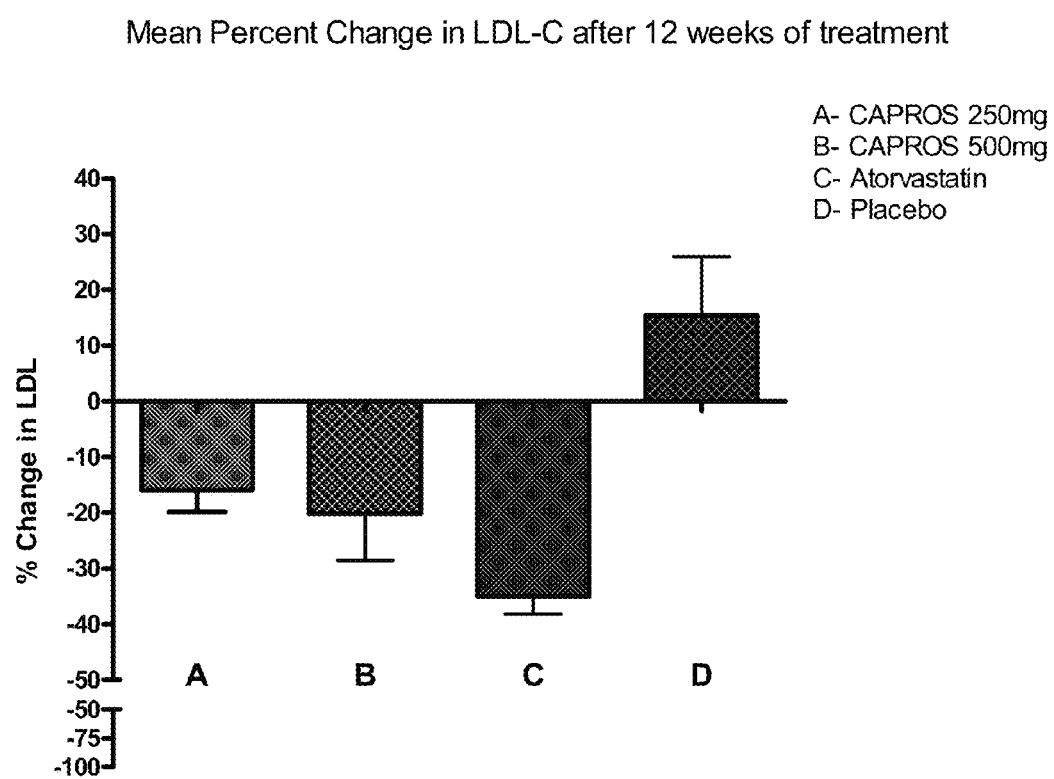
FIG. 8 illustrates mean percent change in LDL-C concentration level in type 2 diabetic individuals before and after 12 weeks treatment in one embodiment in accordance with the present invention with an extract of *Phyllanthus emblica*, or atorvastatin, as described in Table XII-B.
Figure 9:
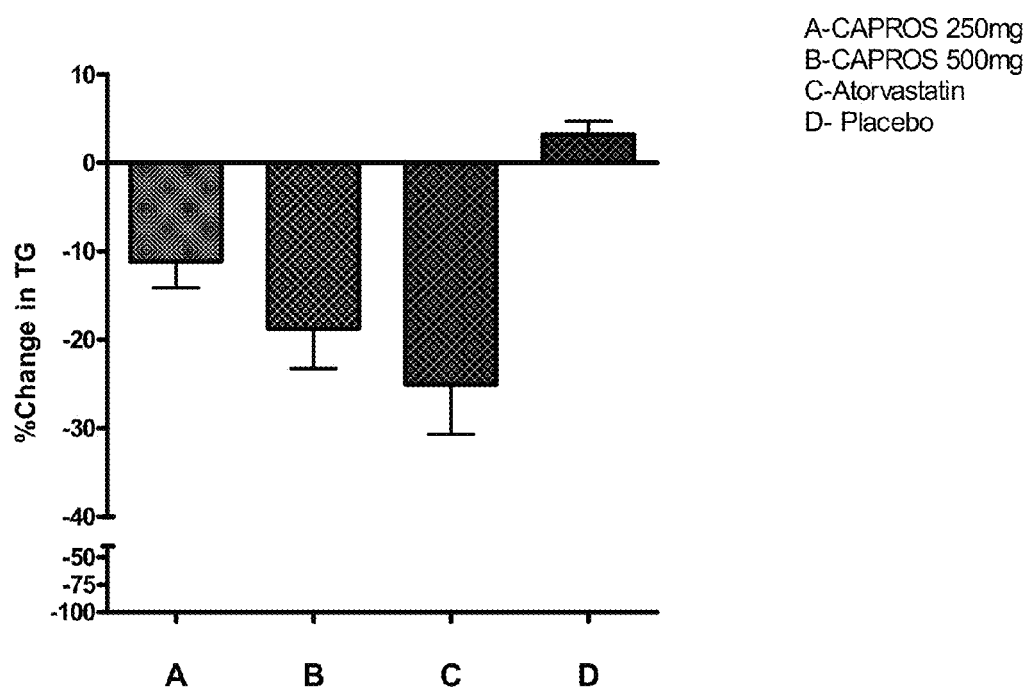
FIG. 9 illustrates mean percent change in triglycerides (TG) concentration level in type 2 diabetic individuals before and after 12 weeks treatment in one embodiment in accordance with the present invention with an extract of *Phyllanthus emblica*, or atorvastatin, as described in Table XII-B.
Figure 10:
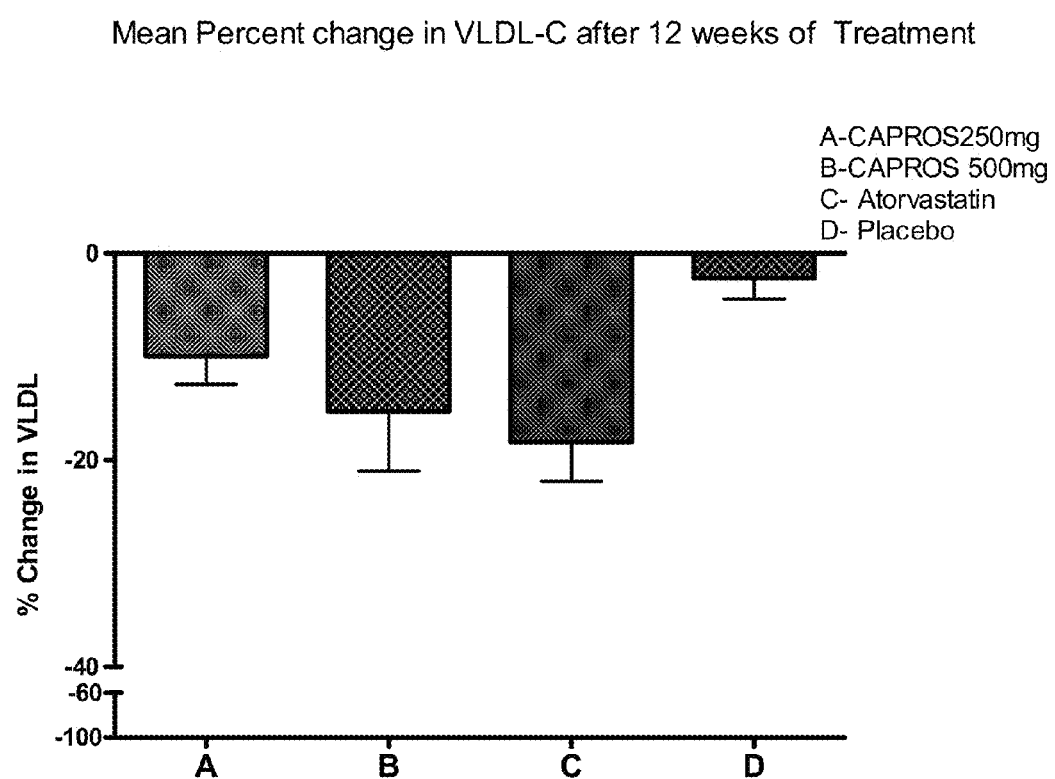
FIG. 10 illustrates mean percent change in VLDL-C concentration level in type 2 diabetic individuals before and after 12 weeks treatment in one embodiment in accordance with the present invention with an extract of *Phyllanthus emblica*, or atorvastatin, as described in Table XII-B.

TC-Nonsignificant when compared between A & B, $p < 0.05$ between B & C, $p < 0.01$ between A & C
$p < 0.001$ when compared between A & D B & D and C & D. (See, FIG. 6.)
HDL-Nonsignificant when compared between A & B, B & C and $p < 0.05$ between A & C
$p < 0.01$ when compared between A & D, $p < 0.001$ when compared between B & D and C & D. (See, FIG. 7.)
LDL-Nonsignificant when compared between A & B and B & C, $p < 0.001$ between A & C
$p < 0.01$ A & D, $p < 0.05$ between B & D, $p < 0.001$ C & D. (See, FIG. 8.)
TG - $p < 0.05$ when compared between A & C, Nonsignificant between A & B, B & C
$p < 0.001$ between A & D, B & D and C& D. (See, FIG. 9.)
VLDL- Nonsignificant when compared between A & B, B & C and between A & C
$p < 0.05$ when compared between A & D and B & D, $p < 0.001$ between C & D. (See, FIG. 10.)

The above Table XII-B includes results that pertain to FIGS. 6-10 which show that after 12 weeks of treatment, an extract of *Phyllanthus emblica* was effective to significantly improve certain lipid levels in a patient suffering from type 2 DM. In particular, levels of total cholesterol (TC), LDL-C, TG, and VLDL-C were observed to decrease significantly in a dose dependent manner, while levels of HDL-C were observed to increase significantly in a dose dependent manner. The observed improvement in these lipid levels was comparable to that observed for patients receiving atorvastatin.

TABLE XIII

Type 2 Diabetic Subjects: Effect of CAPROS ® 250 mg, CAPROS ® 500 mg, Atorvastatin 10 mg and Placebo on Glycosylated Hemoglobin A1c (HbA1c %)

| Parameter | CAPROS ® 250 mg (n = 20) | | CAPROS ® 500 mg (n = 20) | | Atorvastatin (n = 20) | | Placebo (n = 20) | |
|---|---|---|---|---|---|---|---|---|
| | PreTT A | Post TT B | Pre TT C | Post TT D | Pre TT E | Post TT F | Pre TT G | Post TT H |
| HbA1c (%) | 7.79 ± 0.48 | 7.57 ± 0.54 | 7.56 ± 0.5 | 7.09 ± 0.88 | 7.62 ± 0.33 | 6.99 ± 0.39 | 7.64 ± 0.44 | 7.66 ± 0.46 |

Baseline values between the four treatments were comparable
$p < 0.01$ when compared between B & A, D & C
$p < 0.001$ between F&E and nonsignificant when compared between H & G

TABLE XIII-A

Type 2 Diabetic Subjects: Comparison of absolute change between the four treatments on Glycosylated Hemoglobin A1c (HbA1c %)

| Parameter | CAPROS ® 250 mg (n = 20) A | CAPROS ® 500 mg (n = 20) B | Atorvastatin (n = 20) C | Placebo (n = 20) D |
|---|---|---|---|---|
| HbA1c (%) | −0.22 ± 0.32 | −0.47 ± 0.54 | −0.64 ± 0.23 | 0.02 ± 0.27 |

$p < 0.001$ when compared between A & C, Nonsignificant when compared between A & B, B & C
$p < 0.05$ when compared between A & D, $p < 0.001$ between B & D and C & D In the above study treatment with CAPROS® 250 mg, CAPROS® 500 mg and Atorvastatin 10 mg produced significant improvement in mean reflection index (RI) compared to baseline (Tables IX and X-A; FIG. 1). Reduction in (MDA, hs-CRP), and/or elevation of (NO, GSH), the levels of markers of oxidative stress were observed suggesting improvement in endothelial function in diabetic patients (Tables XI, XI-A, XI-B; FIGS. 2-5). The treatment groups also showed significant improvement in the lipid parameters (Tables XII, XII-A, XII-B; FIGS. 6-10) and in the various pharmacodynamic cardiovascular parameters (Tables X and X-A) assessed in diabetic patients. Treatment with CAPROS® 250 mg, CAPROS® 500 mg and Atorvastatin 10 mg showed significant reduction in glycosylated hemoglobin A1c levels compared to baseline and placebo (Tables XIII, XIII-A). All the four treatments were well tolerated. Further compared to 250 mg dose, CAPROS® 500 mg showed a better response in improving endothelial function. Additionally, CAPROS® 500 mg and Atorvastatin showed an increase in response in the levels of biomarkers of oxidative stress and inflammatory biomarker compared to 250 mg dose study.

Study (c) subset (i). Combination of CAPROS®500 with antithrombotic (Clopidogrel).

Inhibition of platelet aggregation using ADP as aggregant on Clopidogrel 75 mg, CAPROS®500 mg, and a combination thereof produced was performed and inhibition of platelet aggregation compared to baseline.

Method for Evaluating Platelet Function.

The effect of CAPROS® 500 mg BD (multiple dose study), Clopidogrel 75 mg (single dose study) and Capros 500 mg+Clopidogrel 75 mg on platelet function was determined by the following procedure using the dual channel platelet aggregometer instrument, as described above. The percentage aggregation at baseline and the percentage inhibition of platelet aggregation on post treatment with all the three treatments was calculated.

Bleeding Time: Bleeding time in seconds was recorded at baseline and at day 10, after 4 hrs post treatment in all the treatment groups by Duke's Method. Normal Range: 60-180 Sec.

Clotting Time: Clotting time in seconds was recorded at baseline and at day 10, after 4 hrs post treatment in all the treatment groups by Capillary Tube Method. Normal Range- 300-480 Sec.

TABLE XIV

Type 2 Diabetic Subjects: Effect of treatments on inhibition of platelet aggregation

| Parameter | Group -I CLOPIDOGREL 75 mg (Single Dose) (Day 1) (n = 10) | Group -II CAPROS ® 500 mg BD (Multiple Dose) (Day 10) (n = 10) | Group -III CAPROS ® 500 mg BD (Multiple Dose) + CLOPIDOGREL 75 mg (Day 11) (n = 10) |
|---|---|---|---|
| Mean | 47.40 | 36.00 | 50.70 |
| SD | ±7.276 | ±10.41 | ±8.247 |

$p < 0.01$ when compared between Clopidogrel 75 mg single dose (Group -I) and Capros 500 mg BD multiple dose (Group -II).

$p < 0.001$ when compared between Capros500 mg BD multiple dose (Group -II) and Capros 500 mg BD multiple dose + Clopidogrel 75 mg (Group -III).

$p < 0.01$ when compared between Clopidogrel 75 mg single dose (Group -I) and Capros 500 mg BD multiple dose + Clopidogrel 75 mg (Group -III).

Figure 11:
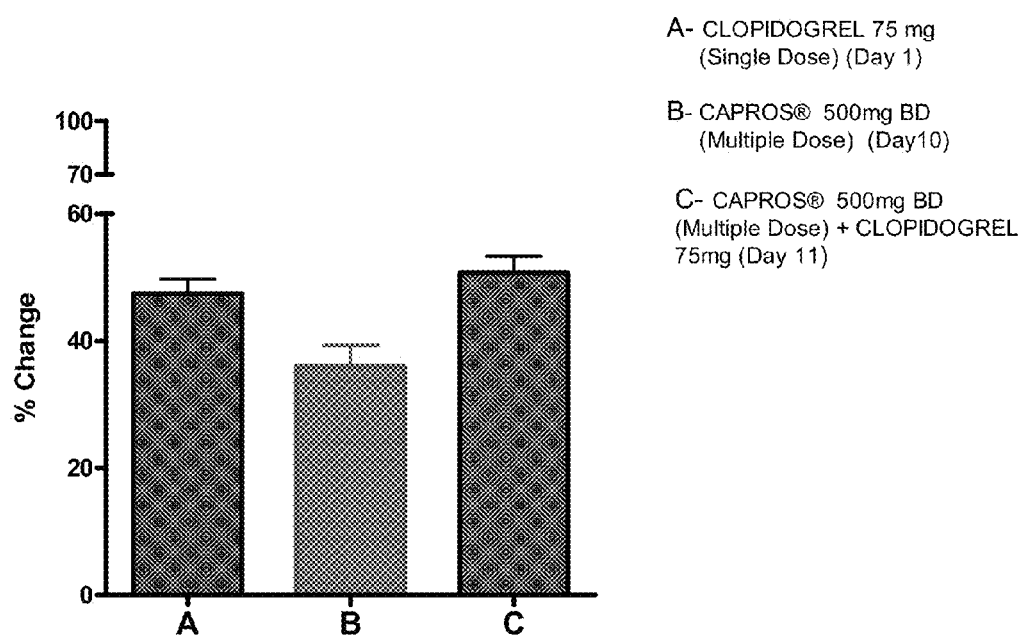
FIG. 11 illustrates mean percent change in inhibition of platelet aggregation using ADP as aggregant on Clopidogrel 75 mg, CAPROS® 500 mg, and a combination of both, in type 2 diabetic individuals in one embodiment in accordance with the present invention using the extract of *Phyllanthus emblica* as described in Table XIV.

Inhibition of platelet aggregation using ADP as aggregant on Clopidogrel 75 mg, CAPROS® 500 mg and combination produced highly significant inhibition of platelet aggregation compared to baseline (Table XIV; FIG. 11). The response in Clopidogrel 75 mg and Clopidogrel 75 mg+CAPROS® 500 mg group was similar suggesting that both the drugs can be used safely without any drug interactions. In an earlier study effect of Atorvastatin on platelet aggregation was evaluated, and compared to CAPROS (at a dosage of 250 mg). See results in Table V above. Atorvastatin did not produce significant reduction with ADP induced platelet aggregation.

The study results demonstrated that CAPROS® 500 mg can provide significant protection from cardiovascular risk factors and showed improvement in cardiovascular parameters including inhibition of platelet aggregation.

TABLE XIV-A

Type 2 Diabetic Subjects: Effect of treatments on Bleeding Time (in Seconds)

| Parameter | Group-I CLOPIDOGREL 75 mg (Single Dose) (Day 1) (n = 10) | | Group-II CAPROS ® 500 mg BD (Multiple Dose) (Day 10) (n = 10) | | Group-III CAPROS ® 500 mg BD (Multiple Dose) + CLOPIDOGREL 75 mg (Day 11) (n = 10) | |
|---|---|---|---|---|---|---|
| | Baseline A | 4$^{th}$ Hr Post treatment B | Baseline C | 4$^{th}$ Hr Post treatment D | Baseline E | 4$^{th}$ Hr Post treatment F |
| Mean | 84.40 | 97.30 | 80.50 | 78.40 | 82.10 | 102.8 |
| SD | ±16.94 | ±26.92 | ±9.744 | ±14.92 | ±14.53 | ±11.35 |

$p < 0.05$ when compared between A & B,
$p < 0.01$ when compared between E & F and D & F
Nonsignificant between A & C, A & E and C & E
Nonsignificant between B & D, B & F and C & D

TABLE XIV-B

Type 2 Diabetic Subjects: Effect of treatments on Bleeding Time (in Seconds)

| Parameter | Group-I CLOPIDOGREL 75 mg (Single Dose) (Day 1) (n = 10) | | Group-II CAPROS ® 500 mg BD (Multiple Dose) (Day 10) (n = 10) | | Group-III CAPROS ® 500 mg BD (Multiple Dose) + CLOPIDOGREL 75 mg (Day 11) (n = 10) | |
|---|---|---|---|---|---|---|
| | Baseline A | 4$^{th}$ Hr Post treatment B | Baseline C | 4$^{th}$ Hr Post treatment D | Baseline E | 4$^{th}$ Hr Post treatment F |
| Mean | 207.5 | 249.5 | 232.3 | 227.9 | 240.5 | 265.5 |
| SD | ±37.78 | ±18.63 | 25.24 | 22.16 | ±34.13 | ±20.81 |

$p < 0.001$ when compared between A & B
$p < 0.01$ between E & F, and D & F
$p < 0.05$ between B & D
Nonsignificant between A & C, A & E, B & F, C & D, C & E The nutraceutical compositions of the present invention may be administered in combination with a nutraceutically acceptable carrier. The active ingredients in such formulations may comprise from 1% by weight to 99% by weight, or alternatively, 0.1% by weight to 99.9% by weight. "Nutraceutically acceptable carrier" means any carrier, diluent or excipient that is compatible with the other ingredients of the formulation and not deleterious to the user. In accordance with one embodiment, suitable nutraceutically acceptable carriers can include ethanol, aqueous ethanol mixtures, water, fruit and/or vegetable juices, and combinations thereof.

The pharmaceutical compositions of the present invention may be administered in combination with a pharmaceutically acceptable carrier. The active ingredients in such formulations may comprise from 1% by weight to 99% by weight, or alternatively, 0.1% by weight to 99.9% by weight. "Pharmaceutically acceptable carrier" means any carrier, diluent or excipient that is compatible with the other ingredients of the formulation and not deleterious to the user.

Delivery System

Suitable dosage forms include tablets, capsules, solutions, suspensions, powders, gums, and confectionaries. Sublingual delivery systems include, but are not limited to, dissolvable tabs under and on the tongue, liquid drops, and beverages. Edible films, hydrophilic polymers, oral dissolvable films or oral dissolvable strips can be used. Other useful delivery systems comprise oral or nasal sprays or inhalers, and the like.

For oral administration, a *Phyllantus emblica* extract may be further combined with one or more solid inactive ingredients for the preparation of tablets, capsules, pills, powders, granules or other suitable dosage forms. For example, the active agent may be combined with at least one excipient such as fillers, binders, humectants, disintegrating agents, solution retarders, absorption accelerators, wetting agents, absorbents, or lubricating agents. Other useful excipients include magnesium stearate, calcium stearate, mannitol, xylitol, sweeteners, starch, carboxymethylcellulose, microcrystalline cellulose, silica, gelatin, silicon dioxide, and the like.

The components of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof many comprise conventional ingredients in conventional proportions, with or without additional active compounds or principles, and such unit dosage forms may contain any suitable effective amount of the active ingredient commensurate with the intended daily dosage range to be employed.

The components of the present invention can be administered in a wide variety of oral and parenteral dosage forms. It will be obvious to those skilled in the art that the following dosage forms may comprise, as the active component, either a chemical compound of the invention or a pharmaceutically acceptable salt of a chemical compound of the invention.

For preparing pharmaceutical compositions from a chemical compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired.

The powders and tablets preferably contain from five or ten to about seventy percent of the active compound(s). Suitable carriers are magnesium carbonate, magnesium state, talc, sugar, lactose, pectin, dextrin, starch, gelatin, tragacanth, methylcellulose, sodium carboxymethlycellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges are included. Tablets, powders, capsules, pills, cachets, and lozenges can be used as solid forms suitable for oral administration.

Liquid preparations include solutions, suspensions, and emulsions, for example, water or water-propylene glycol solutions. For example, parenteral injection liquid preparations can be formulated as solutions in aqueous polyethylene glycol solution. The chemical compound according to the present invention may thus be formulated for parenteral administration (e.g. by injection, for example bolus injection or continuous infusion) and may be presented in unit dose for in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavors, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Compositions suitable for topical administration in the mouth includes lozenges comprising the active agent in a flavored base, usually sucrose and acacia or tragacanth; pastilles comprising the active ingredient in an inert base such as gelatin and glycerine or sucrose and acacia; and mouthwashes comprising the active ingredient in suitable liquid carrier.

Solutions or suspensions are applied directly to the nasal cavity by conventional means, for example with a dropper, pipette or spray. The compositions may be provided in single or multi-dose form. In compositions intended for administration to the respiratory tract, including intranasal compositions, the compound will generally have a small particle size for example of the order of 5 microns or less. Such a particle size may be obtained by means known in the art, for example by micronization.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenges itself, or it can be the appropriate number of any of these in packaged form.

Tablets, capsules and lozenges for oral administration and liquids for oral use are preferred compositions. Solutions or suspensions for application to the nasal cavity or to the respiratory tract are preferred compositions. Transdermal patches for topical administration to the epidermis are preferred.

Further details on techniques for formulation and administration may be found in the latest edition of Remington's Pharmaceutical Sciences (Mack Publishing Co., Easton, Pa.).

Solid nutritional compositions for oral administration may optionally contain, in addition to the above enumerated nutritional composition ingredients or compounds: carrier materials such as corn starch, gelatin, acacia, microcrystalline cellulose, kaolin, dicalcium phosphate, calcium carbonate, sodium chloride, alginic acid, and the like; disintegrators including, microcrystalline cellulose, alginic acid, and the like; binders including acacia, methylcellulose, sodium carboxymethylcellulose, polyvinylpyrrolidone, hydroxypropyl methylcellulose, ethyl cellulose, and the like; and lubricants such as magnesium stearate, stearic acid, silicone fluid, talc, waxes, oils, colloidal silica, and the like. The usefulness of such excipients is well known in the art.

In one preferred embodiment, the nutritional composition may be in the form of a liquid. In accordance with this embodiment, a method of making a liquid composition is provided.

Liquid nutritional compositions for oral administration in connection with a method for preventing and/or treating inflammation, colds and/or flu can be prepared in water or other aqueous vehicles. In addition to the above enumerated ingredients or compounds, liquid nutritional compositions can include suspending agents such as, for example, methylcellulose, alginates, tragacanth, pectin, kelgin, carrageenan, acacia, polyvinylpyrrolidone, polyvinyl alcohol, and the like. The liquid nutritional compositions can be in the form of a solution, emulsion, syrup, gel, or elixir including or containing, together with the above enumerated ingredients or compounds, wetting agents, sweeteners, and coloring and flavoring agents. Various liquid and powder nutritional compositions can be prepared by conventional methods. Various ready-to-drink formulations (RTD's) are contemplated.

Routes of Administration

The compositions may be administered by any suitable route, including but not limited to oral, sublingual, buccal, ocular, pulmonary, rectal, and parenteral administration, or as an oral or nasal spray (e.g. inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of a pharmaceutical composition in the body of the patient in a controlled formulation, with systemic or local release of the drug to occur at a later time. For example, the drug may be localized in a depot for controlled release to the circulation, or for release to a local site.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflations, including powders and liquid aerosol administration, or by sustained release systems. Suitable examples of sustained release systems include semipermeable matrices of solid hydrophobic polymers containing the compound of the invention, which matrices may be in form of shaped artices, e.g. films or microcapsules.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of treating or preventing endothelial dysfunction comprising administering to an individual in need thereof an effective amount of a composition comprising an extract of pulped *Phyllanthus emblica* and a pharmaceutically acceptable carrier, wherein endothelial function is improved.

2. The method according to claim 1 wherein the extract includes at least about 60% by weight low molecular weight hydrolyzable tannoids based on the total weight of the composition.

3. The method according to claim 1 wherein the extract includes greater than about 70% by weight low molecular weight hydrolyzable tannoids based on the total weight of the composition.

4. The method according to claim 2 wherein the improved endothelial function includes an increase of at least about 30% in the blood level of nitric oxide (NO).

5. The method according to claim 2 wherein the composition is administered in a dose of about 250 mg/day to about 1000 mg/day.

6. The method according to claim 2 wherein the low molecular weight hydrolyzable tannoids include emblicanin-A, emblicanin-B, punigluconin, and pedunculagin.

7. A method of treating a diabetic individual suffering from type 2 diabetes mellitus comprising administering to an individual in need thereof an effective amount of an extract of pulped *Phyllanthus emblica*, wherein endothelial function is improved.

8. The method according to claim 7 wherein the extract includes at least about 60% by weight low molecular weight hydrolyzable tannoids based on the total weight of the composition.

9. The method according to claim 7 wherein the extract includes greater than about 70% by weight low molecular weight hydrolyzable tannoids based on the total weight of the composition.

10. The method according to claim 8 wherein the improved endothelial function includes an increase of at least about 30% in the blood level of nitric oxide (NO) in the diabetic individual.

11. The method according to claim 8 wherein the improved endothelial function includes an increase of at least about 50% in the blood level of nitric oxide (NO) in the diabetic individual.

12. The method according to claim 8 wherein the composition is administered in a dose of about 250 mg/day to about 1000 mg/day.

13. The method according to claim 8 wherein the low molecular weight hydrolyzable tannoids include emblicanin-A, emblicanin-B, punigluconin, and pedunculagin.

14. A method of treating a diabetic individual suffering from type 2 diabetes mellitus comprising administering to an individual in need thereof an effective amount of an extract of pulped *Phyllanthus emblica*, wherein a blood lipid parameter is improved.

15. The method according to claim 14 wherein the extract includes at least about 60% by weight low molecular weight hydrolyzable tannoids based on the total weight of the composition.

16. The method according to claim 14 wherein the extract includes greater than about 70% by weight low molecular weight hydrolyzable tannoids based on the total weight of the composition.

17. The method according to claim 15 wherein the improved blood lipid parameter includes a decrease of at least about 10% in the blood level of total cholesterol or LDL-C in the diabetic individual.

18. The method according to claim 15 wherein the improved blood lipid parameter includes an increase of at least about 10% in the blood level of HDL-C in the diabetic individual.

19. The method according to claim 15 wherein the composition is administered in a dose of about 250 mg/day to about 1000 mg/day.

20. The method according to claim 15 wherein the low molecular weight hydrolyzable tannoids include emblicanin-A, emblicanin-B, punigluconin, and pedunculagin.

* * * * *